(12) United States Patent
Skov et al.

(10) Patent No.: US 9,611,469 B2
(45) Date of Patent: Apr. 4, 2017

(54) THERMOSTABLE PHYTASE VARIANTS

(71) Applicant: NOVOZYMES A/S, Bagsvaerd (DK)

(72) Inventors: Lars Kobberoee Skov, Bagsvaerd (DK); Leonardo De Maria, Bagsvaerd (DK); Tomoko Matsui, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 14/627,584

(22) Filed: Feb. 20, 2015

(65) Prior Publication Data

US 2015/0159149 A1    Jun. 11, 2015

Related U.S. Application Data

(63) Continuation of application No. 13/636,197, filed as application No. PCT/EP2011/054639 on Mar. 25, 2011, now abandoned.

(Continued)

(30) Foreign Application Priority Data

Mar. 26, 2010 (EP) .................................... 10158027

(51) Int. Cl.
*C12N 9/96*    (2006.01)
*C12N 9/16*    (2006.01)
(Continued)

(52) U.S. Cl.
CPC ................ *C12N 9/96* (2013.01); *A23K 10/16* (2016.05); *A23L 33/195* (2016.08); *A61K 38/46* (2013.01);
(Continued)

(58) Field of Classification Search
None
See application file for complete search history.

(56) References Cited

U.S. PATENT DOCUMENTS 7,442,398 B2    10/2008    Kim
7,833,768 B2    11/2010    Wik
(Continued)

FOREIGN PATENT DOCUMENTS

WO    2004/085638 A1    10/2004
WO    2006/037328 A1    4/2006
(Continued)

OTHER PUBLICATIONS

Anonymous, GeneSeq Database, Accession No. ADU50737 (1998).
(Continued)

*Primary Examiner* — Robert Mondesi
*Assistant Examiner* — Richard Ekstrom
(74) *Attorney, Agent, or Firm* — Elias Lambris

(57) ABSTRACT

The present invention relates to a method for producing phytase variants which has at least 74% identity to a phytase derived from *Citrobacter braakii* and comprises at least two additional disulfide bonds as compared to this phytase. These phytase variants have modified, preferably improved, properties, such as thermostability, temperature profile, pH profile, specific activity, performance in animal feed, reduced protease sensitiliby, and/or an modified glycosylation pattern. The invention also relates to the variants produced, DNA encoding these phytases, methods of their production, as well as the use thereof, e.g., in animal feed and animal feed additives.

24 Claims, 1 Drawing Sheet

Related U.S. Application Data

(60) Provisional application No. 61/318,001, filed on Mar. 26, 2010.

(51) Int. Cl.

| | | |
|---|---|---|
| *C12P 7/00* | (2006.01) | |
| *A61K 38/46* | (2006.01) | |
| *C12N 15/82* | (2006.01) | |
| *C12P 7/14* | (2006.01) | |
| *C12P 21/00* | (2006.01) | |
| *A23K 10/16* | (2016.01) | |
| *A23L 33/195* | (2016.01) | |

(52) U.S. Cl.
CPC .......... *C12N 9/16* (2013.01); *C12N 15/8243* (2013.01); *C12P 7/00* (2013.01); *C12P 7/14* (2013.01); *C12P 21/00* (2013.01); *C12Y 301/03008* (2013.01); *C12Y 301/03026* (2013.01); *C12Y 301/03072* (2013.01)

(56) References Cited

U.S. PATENT DOCUMENTS

| | | | |
|---|---|---|---|
| 7,867,743 B2 | 1/2011 | Wik | |
| 7,923,232 B2 | 4/2011 | Lassen | |
| 8,076,115 B2 | 12/2011 | Wik | |
| 8,101,391 B2 | 1/2012 | Sjoeholm | |
| 8,143,045 B2 | 3/2012 | Miasnikov | |
| 8,206,962 B2 | 6/2012 | Lassen | |
| 8,334,124 B1 | 12/2012 | Mullaney | |
| 8,409,641 B2 | 4/2013 | Basu | |
| 8,450,096 B2 | 5/2013 | Wik | |
| 8,460,656 B2 | 6/2013 | De Maria | |
| 8,497,127 B2 | 7/2013 | Basu | |
| 8,507,240 B2 | 8/2013 | Lassen | |
| 8,540,984 B2 | 9/2013 | Lei | |
| 2011/0154519 A1 | 6/2011 | Lassen | |
| 2012/0090042 A1 | 4/2012 | Sjoeholm | |
| 2012/0201923 A1 | 8/2012 | Haefner | |
| 2012/0301578 A1 | 11/2012 | Miasnikov | |
| 2013/0017185 A1 | 1/2013 | De Maria | |
| 2013/0040342 A1 | 2/2013 | De Maria | |
| 2013/0108738 A1 | 5/2013 | Haefner | |
| 2013/0122567 A1 | 5/2013 | Blesa | |
| 2013/0136825 A2 | 5/2013 | Miasnikov | |

FOREIGN PATENT DOCUMENTS

| | | |
|---|---|---|
| WO | 2006/038062 A1 | 4/2006 |
| WO | 2006/038128 A2 | 4/2006 |
| WO | 2007/112739 A1 | 10/2007 |
| WO | 2012/110776 A2 | 8/2012 |

OTHER PUBLICATIONS

Guo et al., PNAS, vol. 101, No. 25, pp. 9205-9210 (2004).
Lehmann et al., Biochimica et Biophysica Acta, vol. 1543, No. 2, pp. 408-415 (2000).
Lim et al., Nature Structural Biology, vol. 7, No. 2, pp. 108-113 (2000).
Zinin et al., EMBL Genbank Database, Accession No. AY390262 (2004).
Zinin et al., UniProt Database, Accession No. Q676V7 (2004).

```
SEQ2        1                              EEQNGMKLERVVIVSRHGVRAPTKFTPI      28
                                           ||.||||||||||||||||||||||||
SEQ9        1 MSTFIIRLLFFSLLCGSFSIHAEEPNGMKLERVVIVSRHGVRAPTKFTPI      50

SEQ2       29 MKNVTPDQWPQWDVPLGWLTPRGGELVSELGQYQRLWFTSKGLLNNQTCP      78
              ||:|||||||||||||||||||||||||||||||||||||||||||||||
SEQ9       51 MKDVTPDQWPQWDVPLGWLTPRGGELVSELGQYQRLWFTSKGLLNNQTCP     100

SEQ2       79 SPGQVAVIADTDQRTRKTGEAFLAGLAPKCQIQVHYQKDEEKNDPLFNPV     128
              |||||||||||||||||||||||||||||||||||||||||.|||||||
SEQ9      101 SPGQVAVIADTDQRTRKTGEAFLAGLAPKCQIQVHYQKDEEKTDPLFNPV     150

SEQ2      129 KMGKCSFNTLQVKNAILERAGGNIELYTQRYQSSFRTLENVLNFSQSETC     178
              |||.|||||||:||||||||||||||||||||||||||||||||||||||
SEQ9      151 KMGTCSFNTLKVKNAILERAGGNIELYTQRYQSSFRTLENVLNFSQSETC     200

SEQ2      179 KTTEKSTKCTLPEALPSELKVTPDNVSLPGAWSLSSTLTEIFLLQEAQGM     228
              ||||||||||||||||||||||||||||||||||||||||||||||||||
SEQ9      201 KTTEKSTKCTLPEALPSELKVTPDNVSLPGAWSLSSTLTEIFLLQEAQGM     250

SEQ2      229 PQVAWGRITGEKEWRDLLSLHNAQFDLLQRTPEVARSRATPLLDMIDTAL     278
              ||||||||||||||||||||||||||||||||||||||||||||||||||
SEQ9      251 PQVAWGRITGEKEWRDLLSLHNAQFDLLQRTPEVARSRATPLLDMIDTAL     300

SEQ2      279 LTNGTTENRYGIKLPVSLLFIAGHDTNLANLSGALDLNWSLPGQPDNTPP     328
              ||||||||||||||||||||||||||||||||||||||||||||||||||
SEQ9      301 LTNGTTENRYGIKLPVSLLFIAGHDTNLANLSGALDLNWSLPGQPDNTPP     350

SEQ2      329 GGELVFEKWKRTSDNTDWVQVSFVYQTLRDMRDIQPLSLEKPAGKVDLKL     378
              ||||||||||||||||||||||||||||||||||||||||||||||||||
SEQ9      351 GGELVFEKWKRTSDNTDWVQVSFVYQTLRDMRDIQPLSLEKPAGKVDLKL     400

SEQ2      379 IACEEKNSQGMCSLKSFSRLIKEIRVPECAVTE       411
              |||||||||||||||||||||||||||||||||
SEQ9      401 IACEEKNSQGMCSLKSFSRLIKEIRVPECAVTE       433
```

THERMOSTABLE PHYTASE VARIANTS

CROSS-REFERENCE TO RELATED APPLICATIONS

This application is a continuation of U.S. application Ser. No. 13/636,197 filed Sep. 20, 2012, now abandoned, which is a 35 U.S.C. 371 national application of international application no. PCT/EP2011/054639 filed Mar. 25, 2011, which claims priority or the benefit under 35 U.S.C. 119 of European application no. 10158027.2 filed Mar. 26, 2010 and U.S. provisional application No. 61/318,001 filed Mar. 26, 2010. The contents of each application are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to a method of producing phytase variants which has at least 74% identity to a phytase derived from *Citrobacter braakii* ATCC 51113 and comprises the establishment of at least two disulfide bridges which are not among the four naturally occurring disulfide bridges as compared to this and closely related phytases (i.e., is a variant thereof). The invention also relates to DNA encoding these phytases, the variants produced, as well as the use thereof, e.g., in animal feed and animal feed additives. The mature part of the *Citrobacter braakii* ATCC 51113 phytase is included in the sequence listing as SEQ ID NO:2.

BACKGROUND OF THE INVENTION

Background Art

Phytases are well-known enzymes, as are the advantages of adding them to foodstuffs for animals, including humans. Phytases have been isolated from various sources, including a number of fungal and bacterial strains.

It is an object of the present invention to provide alternative polypeptides having phytase activity (phytases) and polynucleotides encoding the polypeptides. The phytase variants of the invention exhibit modified or altered preferably improved properties as compared to the parent phytase. Non-limiting examples of such properties are: Stability (such as acid-stability, heat-stability, steam stability, pelleting stability, and/or protease stability, in particular pepsin stability), temperature profile, pH profile, specific activity, substrate specificity, performance in animal feed (such as an improved release and/or degradation of phytate), susceptibility to glycation, and/or glycosylation pattern.

As described herein, mutagenesis of a parent polynucleotide encoding a phytase is employed to prepare variant (synthetic) DNAs encoding a phytase having improved properties relative to the phytase encoded by the parent polynucleotide.

A number of three-dimensional structures of phytases of the Histidine acid phosphate (HAP) type are known. (e.g., Lim et al., 2000, *Nature Struct. Biol.* 7: 108-113). From these it has been found that they all have four disulfide bridges located at the position pairs 77/108 133/407 178/187 381/390 (according to the numbering used here). Typically these occupy all the cysteines present in the molecule.

*Citrobacter*

The sequence of the phyA gene from a strain of *Citrobacter freundii* has been submitted by Zinin et al to the EMBL/GenBank/DDBJ databases with accession no. AY390262. The corresponding phytase amino acid sequence is found in the UniProt/TrEMBL databases with accession no. Q676V7. The expected mature part of Q676V7 is included in the present sequence listing as SEQ ID NO:4. The *Citrobacter freundii* Q676V7 phytase comprises the four disulfide bridges indicated above and no further cysteines are present.

WO-2004/085638 (Republic of National Fisheries Research and Development Institute of Korea) discloses, as SEQ ID NO:7, the amino acid sequence of a phytase from *Citrobacter braakii* YH-15, deposited as KCCM 10427. The mature part of this amino acid sequence is included herein as SEQ ID NO:3. This sequence is also found in the database Geneseqp with accession no. ADU50737. The *Citrobacter braakii* YH-15 phytase comprises the four disulfide bridges indicated above and no further cysteines are present.

WO 2006/037328 (Novozymes NS) discloses the wild-type phytase of *Citrobacter braakii* ATCC 51113 (i.e., SEQ ID NO:2 herein), as well as a variant thereof, which is also included in the present sequence listing, viz. as SEQ ID NO:6. The *Citrobacter braakii* ATCC 51113 phytase comprises the four disulfide bridges indicated above and no further cysteines are present.

WO 2006/038062 and WO 2006/038128 (Danisco NS) both disclose the amino acid sequence of the phytase gene of *Citrobacter freundii* P3-42, deposited under accession number NCIMB 41247 and a number of variants thereof. This amino acid sequence is included herein as SEQ ID NO:9. These applications disclose only one substitution in position 233 to a cysteine (S233C) according to the numbering used herein this would be S211C. The *Citrobacter freundii* P3-42 phytase comprises the four disulfide bridges indicated above and no further cysteines are present. The texts of WO 2006/038062 and WO 2006/038128 seem to be identical.

WO 2007/112739 (Novozymes NS) discloses a large number of phytase variants with exemplification using *Citrobacter braakii* ATCC 51113 phytase as parent. WO 2007/112739 indicates inter alia the creation of disulfide bridges.

BRIEF DESCRIPTION OF THE DRAWINGS AND SEQUENCE LISTING

FIG. 1 is an alignment of the phytases of SEQ ID NO:2 and 9.

In the Sequence listing the sequences apply as follows:

| | |
|---|---|
| SEQ ID NO: 1 | *Citrobacter braakii* ATCC 51113 (WO 2006/037328) |
| SEQ ID NO: 2 | *Citrobacter braakii* ATCC 51113 (WO 2006/037328) |
| SEQ ID NO: 3 | *Citrobacter braakii* YH-15 (WO-2004/085638) |
| SEQ ID NO: 4 | *Citrobacter freundii* (UniProt/TrEMBL accession no. Q676V7) |
| SEQ ID NO: 5 | Variant of SEQ ID NO: 2 (18 is Xaa and 323 are Xaa) |
| SEQ ID NO: 6 | Variant of SEQ ID NO: 2 (18 is Gly and 323 is Pro) |
| SEQ ID NO: 7 | *Citrobacter braakii* ATCC 51113 signal peptide |
| SEQ ID NO: 8 | *Citrobacter braakii* ATCC 51113 pro-peptide |
| SEQ ID NO: 9 | *Citrobacter freundii* NCIMB 41247 (WO 2006/038062 and WO 2006/038128) |

SUMMARY OF EXAMPLES

In the specification the following examples are provided:

Example 1: Preparation of variants, and determination of activity
Example 2: Specific activity
Example 3: Screening for temperature stability
Example 4: Thermostability by DSC
Example 5: Temperature profile
Example 6: pH profile
Example 7: Steam Stability
Example 8: Pelleting stability tests
Example 9: Performance in animal feed in an in vitro model for broilers
Example 10: Performance in an in vivo pig trial
Example 11: Calculating percentage of identity and identifying corresponding positions

DESCRIPTION OF THE INVENTION

The present invention relates to a method of producing a variant phytase having at least 74% identity to SEQ ID NO:2 and comprising the establishment of at least two disulfide bridges as compared to SEQ ID NO:2, wherein said two disulfide bridges which are not among the four naturally occurring ones in positions 77/108, 133/407, 178/187, and 381/390 with the numbering as provided in SEQ ID NO:2.

The percentage of identity is determined as described in the section "Phytase Polypeptides, Percentage of Identity".

The position numbers refer to the position numbering of SEQ ID NO:2, as described in the section "Position Numbering." Positions corresponding to these SEQ ID NO:2 position numbers in other phytases are determined as described in the section "Identifying Corresponding Position Numbers."

The at least two disulfide bridges are established in positions selected from the group consisting of the position pairs: A) 52/99; B) 31/177; C) 46/91; D) 141/199; E) 31/176; F) 59/100; and G) 162/247.

It is preferred that the first disulfide bridge is established in the position pair A between the residues in positions 52 and 99, and the second disulfide bridge is established in the position pair B between the residues in positions 31 and 177.

The method of the invention relates to phytase variants wherein the number of established disulfide bridges is 2, 3, 4, 5, 6, and/or 7.

When the number of established disulfide bridges is two the following combinations of position pairs may be created: A+B, A+C, A+D, A+E, A+F, A+G, B+C, B+D, B+E, B+F, B+G, C+D, C+E, C+F, C+G, D+E, D+F, D+G, E+F, E+G, and F+G, wherein A means 52/99; B means 31/177; C means 46/91; D means 141/199; E means 31/176, F means 59/100; and G means 162/247.

If the number of established disulfide bridges is three the following combinations of position pairs may be created: A+B+C, A+B+D, A+B+E, A+B+F, A+B+G, A+C+D, A+C+E, A+C+F, A+C+G, A+D+E, A+D+F, A+D+G, A+E+F, A+E+G, A+F+G, B+C+D, B+C+E, B+C+F, B+C+G, B+D+E, B+D+F, B+D+G, B+E+F, B+E+G, B+F+G, C+D+E, C+D+F, C+D+G, C+E+F, C+E+G, C+F+G, D+E+F, D+E+G, D+F+G, and E+F+G.

It is also foreseen that the following combinations of position pairs: A+B+C+D, A+B+C+E, A+B+C+F, A+B+C+G, A+B+D+E, A+B+D+F, A+B+D+G, A+B+E+F, A+B+E+G, A+B+F+G, A+C+D+E, A+C+D+F, A+C+D+G, A+C+E+F, A+C+E+G, A+C+E+H, A+C+F+G, A+D+E+F, A+D+E+G, A+D+F+G, A+E+F+G, B+C+D+E, B+C+D+F, B+C+D+G, B+C+E+F, B+C+E+G, B+C+F+G, B+D+E+F, B+D+E+G, B+D+F+G, B+E+F+G, C+D+E+F, C+D+E+G, C+D+F+G, C+E+F+G, C+E+F+H, and D+E+F+G are used to establish four disulfide bridges.

When the number of established disulfide bridges is five combinations are selected from the following position pairs: A+B+C+D+E, A+B+C+D+F, A+B+C+D+G, A+B+C+E+F, A+B+C+E+G, A+B+C+F+G, A+B+D+E+F, A+B+D+E+G, A+B+D+F+G, A+B+E+F+G, A+B+F+G+H, A+C+D+E+F, A+C+D+E+G, A+C+D+F+G, A+C+E+F+G, A+D+E+F+G, B+C+D+E+F, B+C+D+E+G, B+C+D+F+G, B+C+E+F+G, B+D+E+F+G, and C+D+E+F+G.

If the number of established disulfide bridges is six combinations are selected from the following position pairs: A+B+C+D+E+F, A+B+C+D+E+G, A+B+C+D+F+G, A+B+C+E+F+G, A+B+D+E+F+G, A+C+D+E+F+G, and B+C+D+E+F+G.

Finally for the establishment of seven disulfide bridges, the following combination of position pairs may be used: A+B+C+D+E+F+G.

In all the above combinations A means 52/99; B means 31/177; C means 46/91; D means 141/199; E means 31/176, F means 59/100; and G means 162/247

According to the method of the invention the phytase variant may further comprise at least one modification in at least one position selected from the following: 1, 2, 3, 4, 5, 6, 24, 31, 35, 41, 45, 46, 52, 53, 55, 56, 57, 59, 60, 64, 66, 73, 74, 75, 76, 79, 80, 81, 82, 83, 84, 87, 90, 91, 94, 100, 104, 105, 106, 107, 109, 111, 114, 115, 116, 117, 118, 119, 120, 121, 122, 123, 124, 126, 129, 130, 132, 134, 136, 137, 138, 139, 142, 146, 148, 154, 155, 157, 161, 162, 164, 167, 171, 173, 175, 176, 177, 179, 180, 181, 182, 183, 184, 185, 186, 188, 190, 193, 196, 200, 202, 203, 205, 207, 211, 213, 215, 217, 218, 223, 231, 239, 240, 241, 247, 252, 254, 257, 266, 273, 276, 279, 280, 281, 282, 283, 284, 285, 286, 289, 294, 299, 300, 308, 314, 316, 321, 324, 330, 331, 336, 338, 339, 340, 344, 345, 348, 351, 355, 361, 362, 363, 364, 369, 371, 372, 373, 375, 379, 385, 386, 392, 406, 409, 410, and 411.

The invention further provides that the above modifications specifically are chosen from the following: 1*, 1H,K,R,Q, 2D, 2*, 3*, 4P, 5P, 6L, 24R,E, 31T,K,N, 35Y, 41P, 45R, 46D,E, 52E,R 53V,Q,K, 53V 55D,I, 56T, 57Y,V, 60P,H,K,R, 66Y, 73D,P, 74P,S,Y,A, 75T, 76G,P, 79F, 80L, 81E, 82E, 83I, 84Y, 87T, 90V,Y, 91P, 100Y, 104I,A, 105F,E, 106A,G, 107D,E,G, 109A,G, 111P, 114H,N,T, 115Q, 116A,E,P,T,Q, 117D,E,K, 118V,I,L,M,T, 119G,K,R,S, 120K,S,T,Q,R 121A,D,M,P,T,V 121I, 122D, 123P,S, 124L,T,V, N126D, K129G 129I,R,P,Q, 130K,V, 132I, 134T 136P, 137P, 138F, 139N, 142D, 146D, 148T 154P,Q,V 155F, 157F, 161P, 164D,E, 167Q, 171T, 173P,T 175L, 177I 179G,I,K,N,Q, 180A,E,G,T, 181 D,G,I,K,L,S,W 182G,N,R,V,H,K,S,Q, 183RA,L,P,S,V,Q, 184RT, 184*, 185A,S, 185*, 186*, 188P, 193F, 196Q, 200K,R, 202N,H, 203D,E,T,L, 205P, 207G,S, 211C, 213A, 215M, 218Q, 223E, 231P, 239Q, 240P, 241Q, 252H,L, 254Y, 257E, 266M, 273L,Q, 276K,R, 279S, 280P, 281H, 282P, 283P, 284P, 285G,N,R, E285Y, 286D,T,K,Q, 289P, 294T, 299L, 300V, 308A, 314G,N, 316D, 321A, 324N, 330D, 331K, 336R, 338N, 339D, 340A,I, 343D, 344S, 345N, 348H, 351Y, 355P, 361V, 362K,R, I362F, I362L, 362M, 363R, 364Q, 369N, 371P, 373T, 375N, 379K,R, 385D 386I, 392I, 406A, 409D,E, 410D,E, and/or 411R,K.

In a further embodiment additionally the eight amino acids in position 179, 180, 181, 182, 183, 184, 185, and 186 have been replaced by QADKP, GEDKP, NGISA, IAGKS, KEKHQ, KEKQQ, KEKKV, or KTDKL.

According to the invention the variants with additional disulfide bridges may further comprise at least one modification selected from the following: 1*, 1*/2*, 1*/2*/3*, 1K, 4P, 5P, 46E, 52E, 53V, 57Y, 76G, 82E, 107D, 107E, 107G, 109A, 111P, 119R, 119K, 121T, 121D, 137P, 161P, 164E, 167Q, 196Q, 200K, 202N, 218Q, 223E, 241Q, 273L, 276R, 276K, 285G, 285N, 286Q, 299L, 314N, 314G, 362R, 362K, 379R, 379K, 385D, 406A, 410D, 410E, 411R, 411K, or the combinations selected from: 55D/331K, 111P/241Q, 179K/ 180E/181K/182H/183Q/184*/185*/186*, 179K/180E/ 181K/182Q/183Q/184*/185*/186*, 179K/180E/181K/ 182K/183V/184*/185*/186*, 179K/180T/181D/182K/ 183L/184*/185*/186*, 114T/115Q/116A/117D/118T/119S/ 120S/121P/122D/123P/124L, and 114T/115Q/116T/117D/ 118T/119S/120S/121P/122D/123P/124L In specific embodiments of the invention the additional disulfide bridges are selected from the group comprising G52C/A99C, N31C/T177C, W46C/Q91C, K141C/V199C, N31C/E176C, G59C/F100C, and/or S162C/S247C.

In further specific embodiments of the method of the invention further specific modifications are E1K, E1Q, E2D, M6L, K24E, K24R, D31K, D31N, D35Y, G45R, G52R, E53K, E53V, V55I, S56T, E57V, Q60H, Q60K, Q60R, F66Y, N73D, N73P, N74P, N74S, N74Y, Q75T, T76G, T76P, S79F, P80L, G81E, V83I, A87T, D90V, D90Y, F100Y, L104I, Y114N, E118V, K120R, T121I, T121P, N126D, K129G, M130K, M130V, T132I, S134T, L138F, K139N, N142D, E146D, A148T, L154Q, L154V, Y155F, S173T, T177I, T181I, T181L, T181S, T181W, E182A, E182G, E182H, E182I, E182N, E182R, E182V, K183P, K183R, S184R, S184T, T185A, T185S, L193F, D202H, N203D, N203E, P207S, S211C, S213A, Q252H, Q252L, Q257E, R266M, L279S, E285Y, N286D, N286T, A300V, G321A, K336R, K338N, T340A, T340I, N343D, T344S, D345N, Q348H, D361V, I362F, I362L, I362M, Q363R, P364Q, K369N, A371P, K373T, D375N, S386I and L392I or a combination of modifications selected from the group consisting of: K24E/Q60H; Q60K/V83I; N126D/T340I; K24E/ L392I; F66Y/Y114N; T132I/P364Q; N73P/N74S; N73P/ N74P; Q75T/T76G; D202H/N203E; Y155F/T177I; Q252L/ Q348H; K24E/N74Y; N126D/L279S; E2D/R266M; E118V/ A300V; K24E/S173T; E53K/N343D; T76P/S213A; L138F/ L193F; Q252L/K373T; G45R/Q257E/N286T; K139N/ P207S/R266M; D31N/D35Y/M130V; F100Y/S134T/ P207S; T177I/S184R/T185S; E1K/K24E/Q60H; E182R/ Q60H/Q363R; T181W/E182N/K183R; T181W/E182H/ K183R; T181W/E182R/K183R; T181W/E182A/K183R; A0T/K129G/N286D; E1K/E53K/F66Y; M130K/N203D/ L279S; S56T/Q252L/S386I; L154Q/T177I/T344S; K24E/ V55I/T181S; K24R/T177I/D345N; G52R/E182G/R266M, A0T/T177I/S184T/T185A, Q60R/F66Y/L104I/I362L, K24E/Q60H/E146D/Q252L, Q60K/T132I/Q257E/N284T, Q60R/D90V/Q252H/T340A, E22D/E57V/N73D/K338N, E1K/M6L/A87T/T121P/I362L, D31N/D35Y/T177I/P207S/ R266M, K24E/Q60H/N126D/T132I/T340I, D31N/D35Y// P207S/R266M/K336R, D31N/D35Y/T132I/P207S/R266M, Y114N/T177I/T181L/E182I/K183P, E1Q/S79F/Q252L/ I362M/K369N, K24E/Q60H/N73D/D90V/K120R/D361V, D31N/D35Y/M130V/P207S/R266M/A371P, D31K/D35Y/ M130V/P207S/R266M/A371P, D31N/D35Y/F66Y/ M130V/P207S/Q257E/N286T, D31N/D35Y/M130V/ E182V/P207S/R266M/A371P, D31N/D35Y/M130V/ T132I/P207S/R266M/A371P, D31N/D35Y/Q60H/G81E/ M130V/P207S/R266M/A371P, K24E/D31N/D35Y/T121I/ M130V/L154V/P207S/R266M/A371P, Q60K/F66Y/N74P/ Q75T/T76G/V83I/Q252H/Q257E/A371P, Q60K/F66Y/ N73P/N74P/Q75T/Q257E/I362L/P364Q/A371P, D31N/ D35Y/E53V/M130V/A148T/P207S/R266M/Q363R/ A371P, Q60K/F66Y/N74P/T76G/Y114N/M130V/Y155F/ T340I/I362F/A371P/D375N, D31N/D35Y/F66Y/N73P/ N74P/N83I/D90V/Y114N/N126D/N142D/Q252H/T340I/ I362L/A371P, D31N/D35Y/Q60K/F66Y/N73P/P80L/N83I/ N117N/N126D/Y155F/Q252H/Q257E/T340I/A371P, and D31N/D35Y/Q60K/F66Y/N74P/T76G/N83I/D90V/Y155F/ Q252L/G321A/T340I/I362L/A371P.

Further specific embodiments of the method of the invention provides specific variants selected from the following: A/B/K129P, A/B/K129Q, A/B/K129I, A/B/K129R, A/B/ P207G, A/B/N203L/P207G, A/B/K129R/N203L, A/B/K129R/N203L/P207G, A/B/K24R, A/B/K24R/K129P, A/B/K24R/K129R/N203L/P207G, A/B/K24R/K129R/N203L, A/B/D, A/D/F66L/R94V/Σa/E182K/K183Q/T185G/K186L/T188S/P190T/P207G/S213G/T217A/K336V, A/D/F66L/R94V/Σa/T188S/P190T/P207G/S213G/T217A/K336V, A/D/L64F/F66L/R94V/K116A/E119S/T188S/P190T/T217A, A/D/F66L/R94V/Σa/T188S/P190T/P207G/S213G/T217A/K336V/Q252W, A/D/F66L/R94V/Σa/T188S/P190T/P207G/S213G/T217A/K336V/Q252Y, A/D/F66L/R94V/Σa/T188S/P190T/P207G/S213G/T217A/K336V/Q252F, A/D/R94V/K116A/E119S/T188S/P190T/T217A, A/B/D/F66L/R94V/Σa/T188S/P190T/P207G/S213G/T217A/K336V, A/B/D/F66L/R94V/Σa/T188S/P190T/P207G/S213G/T217A/K336V/Q252Y, A/B/D/R94V/K116A/E119S/T188S/P190T/T217A, A/D/R94V/K116A/E118T/E119S/K120S/N121R/T188S/P190T/S213G/T217A/K336V, A/D/R94V/K116A/E118T/E119S/K120S/N121R/T188S/P190T/S213G/T217A, A/D/R94V/K116A/E118T/E119S/K120S/T188S/P190T/T217A, B/D/R94V/K116A/E119S/T188S/P190T/T217A, A/D/Σa/E182K/K183Q/T185G/K186L/S213G/T217A/K336V, D/F66L/R94V/Σa/T188S/P190T/P207G/S213G/T217A/K336V, A/D/F66L/R94V/Σa/E182K/K183Q/T185G/K186L/T188S/P190T/P207G/S213G/T217A/K336V, A/D/F66L/R94V/Σa/T188S/P190T/P207G/S213G/T217A/K336V, D/F66L/R94V/Σa/K179N/E182K/K183Q/T185G/K186L/T188S/P190T/P207G/S213G/T217A/K336V, D/F66L/R94V/Σa/E182N/K183Q/T185G/K186L/T188S/P190T/P207G/S213G/T217A/K336V, D/Σb/E182R/K183Q/T185G/K186L/S213G/T217A/K336R, D/F66L/Σb/E182R/K183Q/T185G/K186L/T188S/P190T/S213G/T217A/K336R, D/F66L/Σb/E182R/K183Q/T185G/K186L/T188S/P190T/E196R/S213G/T217A/K336R, D/Σb/E182R/K183Q/T185G/K186L/S213G/T217A/K336R/K393G/R397Q/K400A, D/Σb/E182K/K183Q/T185G/K186L/S213G/T217A/K336V, D/Σc/K183Q/T185G/K186L/S213G/T217A, D/F66L/Σb/E182R/K183Q/T185G/K186L/T188S/P190T/N203L/S213G, D/F66L/R94V/Σd/E182K/K183Q/T185G/K186L/T188S/P190T/P207G/S213G/T217A/K336V, A/D/R94V/K116A/E119S/T188S/P190T/T217A, A/B/D/F66L/R94V/Σa/T188S/P190T/P207G/S213G/T217A/K336V, D/E1*/E2*/K116A/E119S/T217A, D/E1*/E2*/R94V/K116A/E119S/T188S/P190T/T217A, wherein A means G52C/A99C, B means N31C/T177C, C means W46C/Q91C, D means K141C/V199C, E means N31C/E176C, F means G59C/F100C, and G means S162C/S247C; and wherein Σa means the substitution of the fragment TQADTSSR for the fragment YQKDEEKN in positions 114-121, Σb means the substitution of the fragment TQADTSSP for the fragment YQKDEEKN, Σc means the substitution of the fragment TQADTSSN for the fragment YQKDEEKN, Σd means the substitution of the fragment TQADTSS for the fragment YQKDEEKN.

The method of the invention may be used to create a variant of any wildtype or variant phytase. In particular embodiments, it produces a variant of the mature part of a phytase of SEQ ID NO:2, SEQ ID NO:3, SEQ ID NO:4, SEQ ID NO:6, SEQ ID NO:9, or a variant of any one of the phytase variants related to SEQ ID NO:9 and listed in FIG. 1.

The method of the invention may furthermore provide variants that in addition to the additional disulfide bridges comprise a modification (substitution) or a combination of modifications (substitutions) selected from amongst the modifications (substitutions) and combinations of modifications (substitutions) listed in each row of FIG. 1.

The method of the invention may provide a phytase variant having improved properties, such as thermostability, heat-stability, steam stability, temperature profile, pelleting stability, acid-stability, pH profile, and/or protease stability, in particular pepsin stability, specific activity, substrate specificity, performance in animal feed (such as an improved release and/or degradation of phytate), susceptibility to glycation, and/or glycosylation pattern. The variants provided by the invention exhibit especially improved thermal properties, such as thermostability, heat-stability, steam stability, temperature profile, pelleting stability or improved performance in animal feed.

The method of the invention thus relates to phytase variants having improved thermal properties, such as thermostability, heat-stability, steam stability, temperature profile, and/or pelleting stability.

The method of the invention thus relates to phytase variants having improved thermostability.

The method of the invention thus relates to phytase variants having improved heat-stability.

The method of the invention thus relates to phytase variants having improved steam stability.

The method of the invention thus relates to phytase variants having improved temperature profile.

The method of the invention thus relates to phytase variants having improved pelleting stability.

The method of the invention thus relates to phytase variants having improved acid-stability.

The method of the invention thus relates to phytase variants having improved pH profile.

The method of the invention thus relates to phytase variants having improved protease stability, in particular pepsin stability.

The method of the invention thus relates to phytase variants having improved specific activity.

The method of the invention thus relates to phytase variants having improved substrate specificity.

The method of the invention thus relates to phytase variants having improved performance in animal feed (such as an improved release and/or degradation of phytate).

The method of the invention thus relates to phytase variants having improved susceptibility to glycation.

The method of the invention thus relates to phytase variants having improved and/or glycosylation pattern.

The invention further relates to polynucleotide comprising nucleotide sequences which encode the phytase variants produced by the method, nucleic acid constructs comprising the polynucleotides operably linked to one or more control sequences that direct the production of the polypeptide in an expression host, recombinant expression vectors comprising such nucleic acid constructs, and recombinant host cells comprising a nucleic acid construct and/or an expression vector.

The invention further relates to methods for producing phytase variants as provided comprising (a) cultivating a host cell to produce a supernatant comprising the phytase; and (b) recovering the phytase.

The invention also relates to the phytase variants as such with the modifications indicated above.

The invention thus relates to phytase variants having at least 74% identity to SEQ ID NO:2 and comprising at least two disulfide bridges as compared to SEQ ID NO:2, wherein said two disulfide bridges are in addition to the four naturally occurring ones in positions 77/108, 133/407, 178/187, and 381/390 with the numbering as provided in SEQ ID NO:2.

The at least two disulfide bridges are selected from the group consisting of the position pairs: A) 52/99; B) 31/177; C) 46/91; D) 141/199; E) 31/176; F) 59/100; and G) 162/247.

The invention relates to phytase variants wherein the number of disulfide bridges is 6, 7, 8, 9, 10, and/or 11.

When the number of additional disulfide bridges is two the following combinations of position pairs may be present: A+B, A+C, A+D, A+E, A+F, A+G, B+C, B+D, B+E, B+F, B+G, C+D, C+E, C+F, C+G, D+E, D+F, D+G, E+F, E+G, and F+G, wherein A means 52/99; B means 31/177; C means 46/91; D means 141/199; E means 31/176, F means 59/100; and G means 162/247.

If the number of additional disulfide bridges is three the following combinations of position pairs may be present: A+B+C, A+B+D, A+B+E, A+B+F, A+B+G, A+C+D, A+C+E, A+C+F, A+C+G, A+D+E, A+D+F, A+D+G, A+E+F, A+E+G, A+F+G, B+C+D, B+C+E, B+C+F, B+C+G, B+D+E, B+D+F, B+D+G, B+E+F, B+E+G, B+F+G, C+D+E, C+D+F, C+D+G, C+E+F, C+E+G, C+F+G, D+E+F, D+E+G, D+F+G, and E+F+G.

It is also foreseen that the following combinations of position pairs: A+B+C+D, A+B+C+E, A+B+C+F, A+B+C+G, A+B+D+E, A+B+D+F, A+B+D+G, A+B+E+F, A+B+E+G, A+B+F+G, A+C+D+E, A+C+D+F, A+C+D+G, A+C+E+F, A+C+E+G, A+C+E+H, A+C+F+G, A+D+E+F, A+D+E+G, A+D+F+G, A+E+F+G, B+C+D+E, B+C+D+F, B+C+D+G, B+C+E+F, B+C+E+G, B+C+F+G, B+D+E+F, B+D+E+G, B+D+F+G, B+E+F+G, C+D+E+F, C+D+E+G, C+D+F+G, C+E+F+G, C+E+F+H, and D+E+F+G are used for additional four disulfide bridges.

When the number of additional disulfide bridges is five combinations are selected from the following position pairs: A+B+C+D+E, A+B+C+D+F, A+B+C+D+G, A+B+C+E+F, A+B+C+E+G, A+B+C+F+G, A+B+D+E+F, A+B+D+E+G, A+B+D+F+G, A+B+E+F+G, A+B+F+G+H, A+C+D+E+F, A+C+D+E+G, A+C+D+F+G, A+C+E+F+G, A+D+E+F+G, B+C+D+E+F, B+C+D+E+G, B+C+D+F+G, B+C+E+F+G, B+D+E+F+G, and C+D+E+F+G.

If the number of additional disulfide bridges is six combinations are selected from the following position pairs: A+B+C+D+E+F, A+B+C+D+E+G, A+B+C+D+F+G, A+B+C+E+F+G, A+B+D+E+F+G, A+C+D+E+F+G, and B+C+D+E+F+G.

Finally for additional seven disulfide bridges, the following combination of position pairs may be used: A+B+C+D+E+F+G.

In all the above combinations A means 52/99; B means 31/177; C means 46/91; D means 141/199; E means 31/176, F means 59/100; and G means 162/247

According the invention the phytase variant may further comprise at least one modification in at least one position selected from the following: 1, 2, 3, 4, 5, 6, 24, 31, 35, 41, 45, 46, 52, 53, 55, 56, 57, 59, 60, 64, 66, 73, 74, 75, 76, 79, 80, 81, 82, 83, 84, 87, 90, 91, 94, 100, 104, 105, 106, 107, 109, 111, 114, 115, 116, 117, 118, 119, 120, 121, 122, 123, 124, 126, 129, 130, 132, 134, 136, 137, 138, 139, 142, 146, 148, 154, 155, 157, 161, 162, 164, 167, 171, 173, 175, 176, 177, 179, 180, 181, 182, 183, 184, 185, 186, 188, 190, 193, 196, 200, 202, 203, 205, 207, 211, 213, 215, 217, 218, 223, 231, 239, 240, 241, 247, 252, 254, 257, 266, 273, 276, 279, 280, 281, 282, 283, 284, 285, 286, 289, 294, 299, 300, 308, 314, 316, 321, 324, 330, 331, 336, 338, 339, 340, 344, 345, 348, 351, 355, 361, 362, 363, 364, 369, 371, 372, 373, 375, 379, 385, 386, 392, 406, 409, 410, and 411.

The invention further provides that the above modifications specifically are chosen from the following: 1*, 1H,K, R,Q, 2D, 2*, 3*, 4P, 5P, 6L, 24R,E, 31T,K,N, 35Y, 41P, 45R, 46D,E, 52E,R 53V,Q,K, 53V 55D,I, 56T, 57Y,V, 60P,H,K,R, 66Y, 73D,P, 74P,S,Y,A, 75T, 76G,P, 79F, 80L, 81E, 82E, 83I, 84Y, 87T, 90V,Y, 91P, 100Y, 104I,A, 105F,E, 106A,G, 107D,E,G, 109A,G, 111P, 114H,N,T, 115Q, 116A,E,P,T,Q, 117D,E,K, 118V,I,L,M,T, 119G,K,R,S, 120K,S,T,Q,R 121A,D,M,P,T,V 121I, 122D, 123P,S, 124L,T,V, N126D, K129G 129I,R,P,Q, 130K,V, 132I, 134T 136P, 137P, 138F, 139N, 142D, 146D, 148T 154P,Q,V 155F, 157F, 161P, 164D,E, 167Q, 171T, 173P,T 175L, 177I 179G,I,K,N,Q, 180A,E,G,T, 181D,G,I,K,L,S,W 182G,N,R,V,H,K,S,Q, 183RA,L,P,S,V,Q, 184RT, 184*, 185A,S, 185*, 186*, 188P, 193F, 196Q, 200K,R, 202N,H, 203D,E,T,L, 205P, 207G,S, 211C, 213A, 215M, 218Q, 223E, 231P, 239Q, 240P, 241Q, 252H,L, 254Y, 257E, 266M, 273L,Q, 276K,R, 279S, 280P, 281H, 282P, 283P, 284P, 285G,N,R, E285Y, 286D,T,K,Q, 289P, 294T, 299L, 300V, 308A, 314G,N, 316D, 321A, 324N, 330D, 331K, 336R, 338N, 339D, 340A,I, 343D, 344S, 345N, 348H, 351Y, 355P, 361V, 362K,R, I362F, I362L, 362M, 363R, 364Q, 369N, 371P, 373T, 375N, 379K, R, 385D 386I, 392I, 406A, 409D,E, 410D,E, and/or 411R,K.

In a further embodiment additionally the eight amino acids in position 179, 180, 181, 182, 183, 184, 185, and 186 have been replaced by QADKP, GEDKP, NGISA, IAGKS, KEKHQ, KEKQQ, KEKKV, or KTDKL.

According to the invention the variants with additional disulfide bridges may further comprise at least one modification selected from the following: 1*, 1*/2*, 1*/2*/3*, 1K, 4P, 5P, 46E, 52E, 53V, 57Y, 76G, 82E, 107D, 107E, 107G, 109A, 111P, 119R, 119K, 121T, 121D, 137P, 161P, 164E, 167Q, 196Q, 200K, 202N, 218Q, 223E, 241Q, 273L, 276R, 276K, 285G, 285N, 286Q, 299L, 314N, 314G, 362R, 362K, 379R, 379K, 385D, 406A, 410D, 410E, 411R, 411K, or the combinations selected from: 55D/331K, 111P/241Q, 179K/180E/181K/182H/183Q/184*/185*/186*, 179K/180E/181K/182Q/183Q/184*/185*/186*, 179K/180E/181K/182K/183V/184*/185*/186*, 179K/180T/181 D/182K/183L/184*/185*/186*, 14T/115Q/116A/117D/118T/119S/120S/121P/122D/123P/124L, and 114T/115Q/116T/117D/118T/119S/120S/121P/122D/123P/124L In specific embodiments of the invention the additional disulfide bridges are selected from the group comprising G52C/A99C, N31C/T177C, W46C/Q91C, K141C/V199C, N31C/E176C, G59C/F100C, and/or S162C/S247C.

In further specific embodiments of the invention further specific modifications are E1K, E1Q, E2D, M6L, K24E, K24R, D31K, D31N, D35Y, G45R, G52R, E53K, E53V, V55I, S56T, E57Q, Q60H, Q60K, Q60R, F66Y, N73D, N73P, N74P, N74S, N74Y, Q75T, T76G, T76P, S79F, P80L, G81E, V83I, A87T, D90V, D90Y, F100Y, L104I, Y114N, E118V, K120R, T121I, T121P, N126D, K129G, M130K, M130V, T132I, S134T, L138F, K139N, N142D, E146D, A148T, L154Q, L154V, Y155F, S173T, T177I, T181I, T181L, T181S, T181W, E182A, E182G, E182H, E182I, E182N, E182R, E182V, K183P, K183R, S184R, S184T, T185A, T185S, L193F, D202H, N203D, N203E, P207S, S211C, S213A, Q252H, Q252L, Q257E, R266M, L279S, E285Y, N286D, N286T, A300V, G321A, K336R, K338N, T340A, T340I, N343D, T344S, D345N, Q348H, D361V, I362F, I362L, I362M, Q363R, P364Q, K369N, A371P, K373T, D375N, S386I and L392I or a combination of modifications selected from the group consisting of: K24E/Q60H; Q60K/V83I; N126D/T340I; K24E/L392I; F66Y/Y114N; T132I/P364Q; N73P/N74S; N73P/N74P; Q75T/T76G; D202H/N203E; Y155F/T177I; Q252L/Q348H; K24E/N74Y; N126D/L279S; E2D/R266M; E118V/A300V; K24E/S173T; E53K/N343D; T76P/S213A; L138F/L193F; Q252L/K373T; G45R/Q257E/N286T; K139N/P207S/R266M; D31N/D35Y/M130V; F100Y/S134T/P207S; T177I/S184R/T185S; E1K/K24E/Q60H; K24E/Q60H/Q363R; T181W/E182N/K183R; T181W/E182H/K183R; T181W/E182R/K183R; T181W/E182A/K183R; A0T/K129G/N286D; E1K/E53K/F66Y; M130K/N203D/L279S; S56T/Q252L/S386I; L154Q/T177I/T344S; K24E/V55I/T181S; K24R/T177I/D345N; G52R/E182G/R266M, A0T/T177I/S184T/T185A, Q60R/F66Y/L104I/I362L, K24E/Q60H/E146D/Q252L, Q60K/T132I/Q257E/N284T, Q60R/D90V/Q252H/T340A, E22D/E57V/N73D/K338N, E1K/M6L/A87T/T121P/I362L, D31N/D35Y/T177I/P207S/R266M, K24E/Q60H/N126D/T132I/T340I, D31N/D35Y//P207S/R266M/K336R, D31N/D35Y/T132I/P207S/R266M, Y114N/T177I/T181L/E182I/K183P, E1Q/S79F/Q252L/I362M/K369N, K24E/Q60H/N73 D/D90V/K120R/D361V, D31N/D35Y/M130V/P207S/R266M/A371P, D31K/D35Y/M130V/P207S/R266M/A371P, D31N/D35Y/F66Y/M130V/P207S/Q257E/N286T, D31N/D35Y/M130V/E182V/P207S/R266M/A371P, D31N/D35Y/M130V/T132I/P207S/R266M/A371P, D31N/D35Y/Q60H/G81E/M130V/P207S/R266M/A371P, K24E/D31N/D35Y/T121I/M130V/L154V/P207S/R266M/A371P, Q60K/F66Y/N74P/Q75T/T76G/V83I/Q252H/Q257E/A371P, Q60K/F66Y/N73P/N74P/Q75T/Q257E/I362L/P364Q/A371P, D31N/D35Y/E53V/M130V/A148T/P207S/R266M/Q363R/A371P, Q60K/F66Y/N74P/T76G/Y114N/M130V/Y155F/T340I/I362F/A371P/D375N, D31N/D35Y/F66Y/N73P/N74P//V83I/D90V/Y114N/N126D/N142D/Q252H/T340I/I362L/A371P, D31N/D35Y/Q60K/F66Y/N73P/P80L//V83I/Y117N/N126D/Y155F/Q252H/Q257E/T340I/A371P, and D31N/D35Y/Q60K/F66Y/N74P/T76G//V83I/D90V/Y155F/Q252L/G321A/T340I/I362L/A371P.

Further specific embodiments of the invention provide specific variants selected from the following: A/B/K129P, A/B/K129Q, A/B/K129I, A/B/K129R, A/B/P207G, A/B/N203L/P207G, A/B/K129R/N203L, A/B/K129R/N203L/P207G, A/B/K24R, A/B/K24R/K129P, A/B/K24R/K129R/N203L/P207G, A/B/K24R/K129R/N203L, A/B/D, A/D/F66L/R94V/Σa/E182K/K183Q/T185G/K186L/T188S/P190T/P207G/S213G/T217A/K336V, A/D/F66L/R94V/Σa/T188S/P190T/P207G/S213G/T217A/K336V, A/D/L64F/F66L/R94V/K116A/E119S/T188S/P190T/T217A, A/D/F66L/R94V/Σa/T188S/P190T/P207G/S213G/T217A/K336V/Q252W, A/D/F66L/R94V/Σa/T188S/P190T/P207G/S213G/T217A/K336V/Q252Y, A/D/F66L/R94V/Σa/T188S/P190T/P207G/S213G/T217A/K336V/Q252F, A/D/R94V/K116A/E119S/T188S/P190T/T217A, A/B/D/F66L/R94V/Σa/T188S/P190T/P207G/S213G/T217A/K336V, A/B/D/F66L/R94V/Σa/T188S/P190T/P207G/S213G/T217A/K336V/Q252Y, A/B/D/R94V/K116A/E119S/T188S/P190T/T217A, A/D/R94V/K116A/E118T/E119S/K120S/N121R/T188S/P190T/S213G/T217A/K336V, A/D/R94V/K116A/E118T/E119S/K120S/N121R/T188S/P190T/S213G/T217A, A/D/R94V/K116A/E118T/E119S/K120S/T188S/P190T/T217A, B/D/R94V/K116A/E119S/T188S/P190T/T217A, A/D/Σa/E182K/K183Q/T185G/K186L/S213G/T217A/K336V, D/F66L/R94V/Σa/T188S/P190T/P207G/S213G/T217A/K336V, A/D/F66L/

R94V/Σa/E182K/K183Q/T185G/K186L/T188S/P190T/
P207G/S213G/T217A/K336V, A/D/F66L/R94V/Σa/T188S/
P190T/P207G/S213G/T217A/K336V, D/F66L/R94V/Σa/
K179N/E182K/K183Q/T185G/K186L/T188S/P190T/
P207G/S213G/T217A/K336V, D/F66L/R94V/Σa/E182N/
K183Q/T185G/K186L/T188S/P190T/P207G/S213G/
T217A/K336V, D/Σb/E182R/K183Q/T185G/K186L/
S213G/T217A/K336R, D/F66L/Σb/E182R/K183Q/T185G/
K186L/T188S/P190T/S213G/T217A/K336R, D/F66L/Σb/
E182R/K183Q/T185G/K186L/T188S/P190T/E196R/
S213G/T217A/K336R, D/Σb/E182R/K183Q/T185G/
K186L/S213G/T217A/K336R/K393G/R397Q/K400A,
D/Σb/E182K/K183Q/T185G/K186L/S213G/T217A/
K336V, D/Σc/K183Q/T185G/K186L/S213G/T217A,
D/F66L/Σb/E182R/K183Q/T185G/K186L/T188S/P190T/
N203L/S213G, D/F66L/R94V/Σd/E182K/K183Q/T185G/
K186L/T188S/P190T/P207G/S213G/T217A/K336V, A/D/
R94V/K116A/E119S/T188S/P190T/T217A, A/B/D/F66L/
R94V/Σa/T188S/P190T/P207G/S213G/T217A/K336V,
D/E1*/E2*/K116A/E119S/T217A, D/E1*/E2*/R94V/
K116A/E119S/T188S/P190T/T217A,
wherein A means G52C/A99C, B means N31C/T177C, C means W46C/Q91C, D means K141C/V199C, E means N31C/E176C, F means G59C/F100C, and G means S162C/S247C; and wherein Σa means the substitution of the fragment TQADTSSR for the fragment YQKDEEKN in positions 114-121, Σb means the substitution of the fragment TQADTSSP for the fragment YQKDEEKN, Σc means the substitution of the fragment TQADTSSN for the fragment YQKDEEKN, Σd means the substitution of the fragment TQADTSS for the fragment YQKDEEKN.

The phytase variants of the invention may be variants of any wildtype or variant phytase. In particular embodiments, the variants may originate from the mature part of a phytase of SEQ ID NO:2, SEQ ID NO:3, SEQ ID NO:4, SEQ ID NO:6, SEQ ID NO:9, or a variant of any one of the phytase variants related to SEQ ID NO:9 and listed in FIG. 1.

The variants of the invention may furthermore in addition to the additional disulfide bridges comprise a modification (substitution) or a combination of modifications (substitutions) selected from amongst the modifications (substitutions) and combinations of modifications (substitutions) listed in each row of FIG. 1.

The invention further relates to transgenic plants, or plant part, capable of expressing the phytase variants, compositions comprising at least one phytase variant, and (a) at least one fat soluble vitamin; (b) at least one water soluble vitamin; and/or (c) at least one trace mineral. Such compositions may further comprise at least one enzyme selected from the following group of enzymes: amylase, phytase, phosphatase, xylanase, galactanase, alpha-galactosidase, protease, phospholipase, and/or beta-glucanase. the compositions may be animal feed additives that may have a crude protein content of 50 to 800 g/kg and comprising a phytase variant of the invention.

The invention further relates to methods for improving the nutritional value of an animal feed, by adding a phytase variant of the invention to the feed, processes for reducing phytate levels in animal manure by feeding an animal with an effective amount of the feed, methods for the treatment of vegetable proteins, comprising the step of adding a phytase variant to at least one vegetable protein, and the use of a phytase variant of a composition of the invention.

The invention also provides a method for producing a fermentation product such as, e.g., ethanol, beer, wine, comprising fermenting a carbohydrate material in the presence of a phytase variant, a method for producing ethanol comprising fermenting a carbohydrate material in the presence of a phytase variant and producing ethanol.

Strategy for Preparing Variants

The structure of the *C. braakii* ATCC 51113 phytase was built by homology modelling, using as a template the structure of the *E. coli* AppA phytase (Protein Data Bank id.: 1DKO; Lim et al., 2000, *Nat. Struct. Biol.* 2: 108-113).

The structure was subjected to molecular dynamics (MD) simulations and electrostatic calculations. Positions for putative disulfide bridges and prolines were identified, as well as other positions of potential importance as regards the various desirable enzymatic properties. Finally, putative glycosylation sites (stretches of NXT or NXS) were identified.

All these suggestions were evaluated within the framework of the modelled structure and the simulation results, for the thermostability property with particular emphasis at the high temperature end.

The corresponding phytase variants were prepared by methods known in the art and tested as described in the experimental part.

Phytase Polypeptides, Percentage of Identity

In the present context a phytase is a polypeptide having phytase activity, i.e., an enzyme which catalyzes the hydrolysis of phytate (myo-inositol hexakisphosphate) to (1) myo-inositol and/or (2) mono-, di-, tri-, tetra- and/or pentaphosphates thereof and (3) inorganic phosphate.

In the present context the term a phytase substrate encompasses, i.a., phytic acid and any phytate (salt of phytic acid), as well as the phosphates listed under (2) above.

The ENZYME site at the internet (http://www.expasy.ch/enzyme/) is a repository of information relative to the nomenclature of enzymes. It is primarily based on the recommendations of the Nomenclature Committee of the International Union of Biochemistry and Molecular Biology (IUB-MB) and it describes each type of characterized enzyme for which an EC (Enzyme Commission) number has been provided (Bairoch, 2000, The ENZYME database, *Nucleic Acids Res.* 28:304-305). See also the handbook Enzyme Nomenclature from NC-IUBMB, 1992).

According to the ENZYME site, three different types of phytases are known: A so-called 3-phytase (alternative name 1-phytase; a myo-inositol hexaphosphate 3-phosphohydrolase, EC 3.1.3.8), a so-called 4-phytase (alternative name 6-phytase, name based on 1L-numbering system and not 1D-numbering, EC 3.1.3.26), and a so-called 5-phytase (EC 3.1.3.72). For the purposes of the present invention, all three types are included in the definition of phytase.

In a particular embodiment, the phytases of the invention belong to the family of acid histidine phosphatases, which includes the *Escherichia coli* pH 2.5 acid phosphatase (gene appA) as well as fungal phytases such as *Aspergillus awamorii* phytases A and B (EC: 3.1.3.8) (gene phyA and phyB). The histidine acid phosphatases share two regions of sequence similarity, each centered around a conserved histidine residue. These two histidines seem to be involved in the enzymes' catalytic mechanism. The first histidine is located in the N-terminal section and forms a phosphor-histidine intermediate while the second is located in the C-terminal section and possibly acts as proton donor.

In a further particular embodiment, the phytases of the invention have a conserved active site motif, viz. R-H-G-X-R-X-P, wherein X designates any amino acid (see amino acids 16 to 22 of SEQ ID NOs:2, 3, 4, 6 and amino acids 38-44 of SEQ ID NO:9). In a preferred embodiment, the conserved active site motif is R-H-G-V-R-A-P, i.e., amino acids 16-22 (by reference to SEQ ID NO:2) are RHGVRAP.

For the purposes of the present invention the phytase activity is determined in the unit of FYT, one FYT being the amount of enzyme that liberates 1 micro-mol inorganic ortho-phosphate per min. under the following conditions: pH 5.5; temperature 37° C.; substrate: sodium phytate ($C_6H_6O_{24}P_6Na_{12}$) in a concentration of 0.0050 mol/l. Suitable phytase assays are the FYT and FTU assays described in Example 1 of WO 00/20569. FTU is for determining phytase activity in feed and premix. Phytase activity may also be determined using the assays of Example 1 ("Determination of phosphatase activity" or "Determination of phytase activity").

In a particular embodiment the phytase of the invention is isolated. The term "isolated" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

The relatedness between two amino acid sequences is described by the parameter "identity". For purposes of the present invention, the alignment of two amino acid sequences is determined by using the Needle program from the EMBOSS package (http://emboss.org) version 2.8.0. The Needle program implements the global alignment algorithm described in Needleman and Wunsch, 1970, *J. Mol. Biol.* 48: 443-453. The substitution matrix used is BLOSUM62, gap opening penalty is 10, and gap extension penalty is 0.5.

The degree of identity between an amino acid sequence of the present invention ("invention sequence") and the amino acid sequence referred to in the claims (SEQ ID NO:2) is calculated as the number of exact matches in an alignment of the two sequences, divided by the length of the "invention sequence," or the length of the SEQ ID NO:2, whichever is the shortest. The result is expressed in percent identity.

An exact match occurs when the "invention sequence" and SEQ ID NO:2 have identical amino acid residues in the same positions of the overlap (in the alignment example below this is represented by "I"). The length of a sequence is the number of amino acid residues in the sequence (e.g., the length of amino acids 1-411 of SEQ ID NO:2 is 411).

Example 11 is an example of an alignment of the phytase of SEQ ID NO:2 and the phytase of SEQ ID NO:9, and the example illustrates how to calculate the percentage of identity between these two backbones.

In another, purely hypothetical, alignment example below, the overlap is the amino acid sequence "HTWGER-NL" of Sequence 1; or the amino acid sequence "HGWGEDANL" of Sequence 2. In the example a gap is indicated by a "-".

Hypothetical Alignment Example:

```
Sequence 1: ACMSHTWGER-NL
              | ||| ||
Sequence 2:   HGWGEDANLAMNPS
```

In a particular embodiment, the percentage of identity of an amino acid sequence of a polypeptide with, or to, SEQ ID NO:2 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage.

In the above hypothetical example, the number of exact matches is 6, the length of the shortest one of the two amino acid sequences is 12; accordingly the percentage of identity is 50%.

In particular embodiments of the phytase of the invention, the degree of identity to SEQ ID NO:2 is at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least 99%. In still further particular embodiments, the degree of identity is at least 98.0%, 98.2%, 98.4%, 98.6%, 98.8%, 99.0%, 99.1%, 99.2%, 99.3%, 99.4%, 99.5%, 99.6%, 99.7%, 99.8%, or at least 99.9%. In alternative embodiments, the degree of identity is at least 70%, 71%, 72%, or at least 73%.

In still further particular embodiments, the phytase of the invention has no more than 1, 2, 3, 4, 5, 6, 7, 8, 9, or no more than 10 modifications as compared to SEQ ID NO:2 or any other parent phytase; no more than 11, 12, 13, 14, 15, 16, 17, 18, 19, or no more than 20 modifications as compared to SEQ ID NO:2 or any other parent phytase; no more than 21, 22, 23, 24, 25, 26, 27, 28, 29, or no more than 30 modifications as compared to SEQ ID NO:2 or any other parent phytase; no more than 31, 32, 33, 34, 35, 36, 37, 38, 39, or not more than 40 modifications as compared to SEQ ID NO:2 or any other parent phytase; no more than 41, 42, 43, 44, 45, 46, 47, 48, 49, or no more than 50 modifications as compared to SEQ ID NO:2 or any other parent phytase; no more than 51, 52, 53, 54, 55, 56, 57, 58, 59, or no more than 60 modifications as compared to SEQ ID NO:2 or any other parent phytase; no more than 61, 62, 63, 64, 65, 66, 67, 68, 69, or no more than 70 modifications as compared to SEQ ID NO:2 or any other parent phytase; no more than 71, 72, 73, 74, 75, 76, 77, 78, 79, or no more than 80 modifications as compared to SEQ ID NO:2 or any other parent phytase; no more than 81, 82, 83, 84, 85, 86, 87, 88, 89, or no more than 90 modifications as compared to SEQ ID NO:2 or any other parent phytase; no more than 91, 92, 93, 94, 95, 96, 97, 98, 99, or no more than 100 modifications as compared to SEQ ID NO:2 or any other parent phytase; no more than 101, 102, 103, 104, 105, 106, 107, 108, 109, or no more than 110 modifications as compared to SEQ ID NO:2 or any other parent phytase; no more than 111, 112, 113, 114, 115, 116, 117, 118, 119, or no more than 120 modifications as compared to SEQ ID NO:2 or any other parent phytase; or no more than 121, 122, 123, or 124 modifications as compared to SEQ ID NO:2 or any other parent phytase.

Position Numbering

The nomenclature used herein for defining amino acid positions is based on the amino acid sequence of the phytase derived from *Citrobacter braakii* ATCC 51113, the mature sequence of which is given in the sequence listing as SEQ ID NO:2 (amino acids 1-411 of SEQ ID NO:2). Accordingly, in the present context, the basis for numbering positions is SEQ ID NO:2 starting with E1 and ending with E411.

When used herein the term "mature" part (or sequence) refers to that part of the polypeptide which is secreted by a cell which contains, as part of its genetic equipment, a polynucleotide encoding the polypeptide. In other words, the mature polypeptide part refers to that part of the polypeptide which remains after the signal peptide part, as well as a propeptide part, if any, has been cleaved off. The signal peptide part can be predicted by programs known in the art (e.g., SignalP). The expected signal peptide part of SEQ ID NO:2 is included in the present sequence listing as SEQ ID NO:8, which is encoded by SEQ ID NO:7. SEQ ID NO:2 is the expected mature part. Generally, the first amino acid of the mature part of an enzyme can be determined by N-terminal sequencing of the purified enzyme. Any difference between the signal peptide part and the mature part must then be due to the presence of a propeptide.

Modifications, such as Substitutions, Deletions, Insertions

A phytase variant can comprise various types of modifications relative to a template (i.e., a reference or comparative amino acid sequence such as SEQ ID NO:2): An amino acid can be substituted with another amino acid; an amino acid can be deleted; an amino acid can be inserted; as well as any combination of any number of such modifications. In the present context the term "insertion" is intended to cover also N- and/or C-terminal extensions.

The general nomenclature used herein for a single modification is the following: XDcY, where "X" and "Y" independently designate a one-letter amino acid code, or a "*" (deletion of an amino acid), "D" designates a number, and "c" designates an alphabetical counter (a, b, c, and so forth), which is only present in insertions. Reference is made to Table 1 below which describes purely hypothetical examples of applying this nomenclature to various types of modifications.

often and/or. E.g., the first comma in the listing "53V,Q, 121D, and/or 167Q" denotes an alternative (V or Q), whereas the two next commas should be interpreted as and/or options: 53 V or Q, and/or 121 D, and/or 167Q.

In the present context, "at least one" (e.g., modification) means one or more, e.g., 1, 2, 3, 4, 5, 6, 7, 8, 9, or 10 modifications; or 12, 14, 15, 16, 18, 20, 22, 24, 25, 28, or 30 modifications; and so on, up to a maximum number of modifications of 125, 130, 140, 150, 160, 170, 180, 190, or of 200. The phytase variants of the invention, however, still have to be at least 74% identical to SEQ ID NO:2, this percentage being determined as described above.

A substitution or extension without any indication of what to substitute or extend with refers to the insertion of any natural, or non-natural, amino acid, except the one that occupies this position in the template.

Example 11 provides further illustration of how to apply this nomenclature.

Identifying Corresponding Position Numbers

As explained above, the mature phytase of *Citrobacter braakii* ATCC 51113 (SEQ ID NO:2) is used as the standard for position numbering and, thereby, also for the nomenclature.

For another phytase, in particular a phytase variant of the invention, the position corresponding to position D in SEQ ID NO:2 is found by aligning the two sequences as specified above in the section entitled "Phytase polypeptides, percent-

TABLE 1

| Type | Description | Example |
| --- | --- | --- |
| Substitution | X = Amino acid in template<br>D = Position in template<br>c empty<br>Y = Amino acid in variant | G80A<br>80<br>AALNNSIGVLGVAPSAELYAVKVLGASGSG<br>∥∥∥∥:∥∥∥∥∥∥∥∥∥∥∥∥∥∥∥∥∥<br>AALNNSIAVLGVAPSAELYAVKVLGASGSG |
| Insertion | X = "*"<br>D = Position in template before the insertion<br>c = "a" for first insertion at this position, "b" for next, etc | *80aT *80bY *85aS<br>80    85<br>AALNNSIG..VLGVA.PSAELYAVKVLGASG<br>∥∥∥∥∥∥∥ ∥∥∥∥ ∥∥∥∥∥∥∥∥∥∥∥∥<br>AALNNSIGTYVLGVASPSAELYAVKVLGASG |
| Deletion | X = Amino acid in template<br>D = Position in template<br>c empty<br>Y = "*" | V81*<br>80<br>AALNNSIGVLGVAPSAELYAVKVLGASGSG<br>∥∥∥∥∥∥∥∥ ∥∥∥∥∥∥∥∥∥∥∥∥∥∥∥<br>AALNNSIG.LGVAPSAELYAVKVLGASGSG |
| N-terminal extension | Insertions at position "0". | *0aA *0bT *0cG<br>1<br>...AQSVPWGISRVQ<br>∥∥∥∥∥∥∥∥∥∥∥<br>ATGAQSVPWGISRVQ |
| C-terminal extension | Insertions after the N-terminal amino acid. | *275aS *275bT<br>270 275<br>ATSLGSTNLYGSGLVNAEAATR..<br>∥∥∥∥∥∥∥∥∥∥∥∥∥∥∥∥∥∥∥<br>ATSLGSTNLYGSGLVNAEAATRST |

As explained above, the position number ("D") is counted from the first amino acid residue of SEQ ID NO:2.

Several modifications in the same sequence are separated by "/" (slash), e.g., the designation "1*/2*/3*" means that the amino acids in position number 1, 2, and 3 are all deleted, and the designation "104A/105F" means that the amino acid in position number 104 is substituted by A, and the amino acid in position number 105 is substituted by F.

Alternative modifications are separated by "," (comma), e.g., the designation "119R,K" means that the amino acid in position 119 is substituted with R or K.

The commas used herein in various other enumerations of possibilities mean what they usually do grammatically, viz.

age of identity". From the alignment, the position in the sequence of the invention corresponding to position D of SEQ ID NO:2 can be clearly and unambiguously identified (the two positions on top of each other in the alignment).

Example 11 is an example of an alignment of the phytase of SEQ ID NO:2 and the phytase of SEQ ID NO:9, and the example illustrates how corresponding positions in these two backbones are identified.

Below some additional, purely hypothetical, examples are included which are derived from Table 1 above which in the third column includes a number of alignments of two sequences:

Consider the third cell in the first row of Table 1: The upper sequence is the template, the lower the variant. Position number 80 refers to amino acid residue G in the template. Amino acid A occupies the corresponding position in the variant. Accordingly, this substitution is designated G80A.

Consider now the third cell in the second row of Table 1: The upper sequence is again the template and the lower the variant. Position number 80 again refers to amino acid residue G in the template. The variant has two insertions, viz. TY, after G80 and before V81 in the template. Whereas the T and Y of course would have their own "real" position number in the variant amino acid sequence, for the present purposes we always refer to the template position numbers, and accordingly the T and the Y are said to be in position number 80a and 80b, respectively.

Finally, consider the third cell in the last row of Table 1: Position number 275 refers to the last amino acid of the template. A C-terminal extension of ST are said to be in position number 275a and 275b, respectively, although, again, of course they have their own "real" position number in the variant amino acid sequence.

Modified Properties, Reference Phytase

In a particular embodiment, the method of the invention for producing phytase variants provides variants having modified, preferably improved, properties.

The terms "modified" and "improved" imply a comparison with another phytase. Examples of such other, reference, or comparative, phytases are: SEQ ID NO:2 and/or SEQ ID NO:6. Still further examples of reference phytases may be SEQ ID NO:3, and/or SEQ ID NO:4. A still further example of a reference phytase may be SEQ ID NO:9, and variants thereof.

Non-limiting examples of properties that are modified, preferably improved, are the following: Thermostability, pH profile, specific activity, performance in animal feed, pelleting stability, protease-sensibility, and/or glycosylation pattern. The phytase variants produced by the method of the invention exhibits improved thermostability and may also have a modified, preferably improved, temperature profile, and/or it may incorporate a change of a potential protease cleavage site.

Thermal Performance

Temperature-Stability

Temperature stability may be determined as described in Example 3 by determining the activity during 30 minutes incubation at temperatures from 60° C. or higher and comparing with a reference experiment performed at 37° C.

Thermostability

Thermostability may be determined as described in Example 4, i.e., using DSC measurements to determine the denaturation temperature, Td, of the purified phytase protein. The Td is indicative of the thermostability of the protein: The higher the Td, the higher the thermostability. Accordingly, in a preferred embodiment, the phytase of the invention has a Td which is higher than the Td of a reference phytase, wherein Td is determined on purified phytase samples (preferably with a purity of at least 90% or 95%, determined by SDS-PAGE).

Heat-Stability

Heat stability may be determined as described in Example 5 by determining the temperature/activity profile of the variant phytases.

Steam Stability

Steam stability may be determined as described in Example 7 by determining the residual activity of phytase molecules after steam treatment at 85° C. or 90° C. for a short time.

Pelleting Stability

Pelleting stability may be determined as described in Example 8 by using enzyme granulate pre-mixed with feed. This premix is mixed with feed. From the mixer the feed is conditioned with steam to 95° C. After conditioning the feed is pressed to pellets and the residual activity determined.

In preferred embodiments, the thermal properties such as heat-stability, temperature stability, thermostability, steam stability, and/or pelleting stability as provided by the residual activity, Td or other parameter of the phytase of the invention is higher than the corresponding value, such as the residual activity or Td, of the phytase of SEQ ID NO:2, more preferably at least 101% thereof, or at least 102%, 103%, 104%, 105%, 106%, 107%, 108%, 109%, or at least 110% thereof. Even more preferably, the value of the parameter, such as residual activity or Td, of the phytase of the invention is at least 120%, 130%, 140%, 150%, 160%, 170%, 180%, or at least 190% of the value for the phytase of SEQ ID NO:2.

In still further particular embodiments, the thermostable phytase of the invention has a melting temperature, Tm (or a denaturation temperature, Td), as determined using Differential Scanning calorimetry (DSC) as described in the Examples (i.e., in 20 mM sodium acetate, pH 4.0), of at least 50° C. In still further particular embodiments, the Tm is at least 51, 52, 53, 54, 55, 56, 57, 58, 59, 60, 61, 62, 62.5, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or at least 100° C. DSC measurements may also be performed as described in the Examples.

Temperature Profile/Temperature Stability

Whether or not a phytase of the invention has a modified temperature profile as compared to a reference phytase may be determined as described in Example 5. Accordingly, in a particular embodiment the phytase of the invention has a modified temperature profile as compared to a reference phytase, wherein the temperature profile is determined as phytase activity as a function of temperature on sodium phytate at pH 5.5 in the temperature range of 20-90° C. (in 10° C. steps). A preferred buffer is in 0.25 M Na-acetate buffer pH 5.5. The activity at each temperature is preferably indicated as relative activity (in %) normalized to the value at optimum temperature. The optimum temperature is that temperature within the tested temperatures (i.e., those with 5-10° C. jumps) where the activity is highest.

pH Profile

Whether or not a phytase of the invention has an altered pH profile as compared to a reference phytase may be determined as described in the Examples. Accordingly, in a particular embodiment the phytase of the invention has an altered pH profile as compared to a reference phytase, wherein the pH profile is determined as phytase activity as a function of pH on sodium phytate at 37° C. in the pH range of 2.0 to 7.5 (in 0.5 pH-unit steps). A preferred buffer is a cocktail of 50 mM glycine, 50 mM acetic acid and 50 mM Bis-Tris. The activity at each pH is preferably indicated as relative activity (in %) normalized to the value at optimum pH.

An example of an altered pH profile is where the pH curve (relative activity as a function of pH) is shifted towards higher, or lower, pH. Preferred substitutions which provide a shift of 0.5 pH units towards a higher pH as compared to the reference phytase of SEQ ID NO:2. However, for certain purposes it may be preferred to provide a shift of 0.5 pH units towards a lower pH as compared to the reference phytase of SEQ ID NO:2.

Another example of an altered pH profile is where the optimum pH is changed, in the upward or the downward direction.

In a particular embodiment, the phytase of the invention has an altered pH profile as compared to a reference phytase. More in particular, the pH profile is modified in the pH-range of 3.5-5.5. Still more in particular, the activity at pH 4.0, 4.5, 5.0, and/or 5.5 is at a level of at least 50%, 55%, 60%, 65%, 70%, 75%, 80%, 85%, 90%, or at least 95% of the activity at the pH-optimum.

Specific Activity

In a particular embodiment, the phytase of the invention has an improved specific activity relative to a reference phytase. More in particular, the specific activity of a phytase of the invention is at least 105%, relative to the specific activity of a reference phytase determined by the same procedure. In still further particular embodiments, the relative specific activity is at least 110, 115, 120, 125, 130, 140, 145, 150, 160, 170, 180, 190, 200, 220, 240, 260, 280, 300, 350 or even 400%, still relative to the specific activity of the reference phytase as determined by the same procedure.

In the alternative, the term high specific activity refers to a specific activity of at least 200 FYT/mg Enzyme Protein (EP). In particular embodiments, the specific activity is at least 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900 or 3000 FYT/mg EP.

Specific activity is measured on highly purified samples (an SDS poly acryl amide gel should show the presence of only one component). The enzyme protein concentration may be determined by amino acid analysis, and the phytase activity in the units of FYT, determined as described in Example 1. Specific activity is a characteristic of the specific phytase variant in question, and it is calculated as the phytase activity measured in FYT units per mg phytase variant enzyme protein. See the Examples for further details.

Performance in Animal Feed

In a particular embodiment the phytase of the invention has an improved performance in animal feed as compared to a reference phytase. The performance in animal feed may be determined by the in vitro model indicated in the Examples. Accordingly, in a preferred embodiment the phytase of the invention has an improved performance in animal feed, wherein the performance is determined in an in vitro model, by preparing feed samples composed of 30% soybean meal and 70% maize meal with added CaCl2 to a concentration of 5 g calcium per kg feed; pre-incubating them at 40° C. and pH 3.0 for 30 minutes followed by addition of pepsin (3000 U/g feed) and phytase; incubating the samples at 40° C. and pH 3.0 for 60 minutes followed by pH 4.0 for 30 minutes; stopping the reactions; extracting phytic acid and inositol-phosphates by addition of HCl to a final concentration of 0.5 M and incubation at 40° C. for 2 hours, followed by one freeze-thaw cycle and 1 hour incubation at 40° C.; separating phytic acid and inositol-phosphates by high performance ion chromatography; determining the amount of residual phytate phosphorus (IP6-P); calculating the difference in residual IP6-P between the phytase-treated and a non-phytase-treated blank sample (this difference is degraded IP6-P); and expressing the degraded IP6-P of the phytase of the invention relative to degraded IP6-P of the reference phytase.

The phytase of the invention and the reference phytase are of course dosed in the same amount, preferably based on phytase activity units (FYT). A preferred dosage is 125 FYT/kg feed. Another preferred dosage is 250 FYT/kg feed. The phytases may be dosed in the form of purified phytases, or in the form of fermentation supernatants. Purified phytases preferably have a purity of at least 95%, as determined by SDS-PAGE.

In preferred embodiments, the degraded IP6-P value of the purified phytase of the invention, relative to the degraded IP6-P value of the reference phytase, is at least 101%, or at least 102%, 103%, 104%, 105%, 110%, 115%, or at least 120%. In still further preferred embodiments, the degraded IP6-P value of the purified phytase of the invention, relative to the degraded IP6-P value of the reference phytase, is at least 125%, 130%, 140%, 150%, 160%, 170%, 180%, 190%, or at least 200%. Preferably, the degraded IP6-P value of the phytase of the invention, relative to the degraded IP6-P value of the SEQ ID NO:2 phytase, is at least 105%, 110%, 113%, 115%, 120%, 125%, or at least 130%.

The relative performance of a phytase of the invention may also be calculated as the percentage of the phosphorous released by the reference phytase.

In a still further particular embodiment, the relative performance of the phytase of the invention may be calculated as the percentage of the phosphorous released by the phytase of the invention, relative to the amount of phosphorous released by the reference phytase.

In still further particular embodiments, the relative performance of the phytase of the invention is at least 105%, preferably at least 110, 120, 130, 140, 150, 160, 170, 180, 190, or at least 200%.

Steam Stability

Thermostability is an important parameter, but associated with that also steam stability is important. In this respect reference is made to Example 8 below.

Low-Allergenic Variants

In a specific embodiment, the phytase variants produced by the method of the present invention are (also) low-allergenic variants, designed to invoke a reduced immunological response when exposed to animals, including man. The term immunological response is to be understood as any reaction by the immune system of an animal exposed to the phytase variant. One type of immunological response is an allergic response leading to increased levels of IgE in the exposed animal. Low-allergenic variants may be prepared using techniques known in the art. For example the phytase variant may be conjugated with polymer moieties shielding portions or epitopes of the phytase variant involved in an immunological response. Conjugation with polymers may involve in vitro chemical coupling of polymer to the phytase variant, e.g., as described in WO 96/17929, WO 98/30682, WO 98/35026, and/or WO 99/00489. Conjugation may in addition or alternatively thereto involve in vivo coupling of polymers to the phytase variant. Such conjugation may be achieved by genetic engineering of the nucleotide sequence encoding the phytase variant, inserting consensus sequences encoding additional glycosylation sites in the phytase variant and expressing the phytase variant in a host capable of glycosylating the phytase variant, see, e.g., WO 00/26354. Another way of providing low-allergenic variants is genetic engineering of the nucleotide sequence encoding the phytase variant so as to cause the phytase variants to self-oligomerize, effecting that phytase variant monomers may shield the epitopes of other phytase variant monomers and thereby lowering the antigenicity of the oligomers. Such products and their preparation is described in, e.g., WO 96/16177.

Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the phytase variant by known gene manipulation techniques such as site directed mutagenesis (see, e.g., WO 00/26230, WO 00/26354 and/or WO 00/22103) and/or conjugation of a polymer may be done in sufficient proximity to the epitope for the polymer to shield the epitope.

Nucleic Acid Sequences and Constructs

The present invention also relates to nucleic acid sequences comprising a nucleic acid sequence which encodes a phytase variant of the invention.

The term "isolated nucleic acid sequence" refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The nucleic acid sequences of the invention can be prepared by introducing at least one mutation into a template phytase coding sequence or a subsequence thereof, wherein the mutant nucleic acid sequence encodes a variant phytase. The introduction of a mutation into the nucleic acid sequence to exchange one nucleotide for another nucleotide may be accomplished by any of the methods known in the art, e.g., by site-directed mutagenesis, by random mutagenesis, or by doped, spiked, or localized random mutagenesis.

Random mutagenesis is suitably performed either as localized or region-specific random mutagenesis in at least three parts of the gene translating to the amino acid sequence shown in question, or within the whole gene. When the mutagenesis is performed by the use of an oligonucleotide, the oligonucleotide may be doped or spiked with the three non-parent nucleotides during the synthesis of the oligonucleotide at the positions which are to be changed. The doping or spiking may be performed so that codons for unwanted amino acids are avoided. The doped or spiked oligonucleotide can be incorporated into the DNA encoding the phytase enzyme by any technique, using, e.g., PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints.

The random mutagenesis may be advantageously localized to a part of the parent phytase in question. This may, e.g., be advantageous when certain regions of the enzyme have been identified to be of particular importance for a given property of the enzyme.

Alternative methods for providing variants of the invention include gene shuffling, e.g., as described in WO 95/22625 or in WO 96/00343, and the consensus derivation process as described in EP 897985.

Nucleic Acid Constructs

A nucleic acid construct comprises a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

The term "control sequences" is defined herein to include all components, which are necessary or advantageous for the expression of a polynucleotide encoding a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" denotes herein a configuration in which a control sequence is placed at an appropriate position relative to the coding sequence of the polynucleotide sequence such that the control sequence directs the expression of the coding sequence of a polypeptide.

When used herein the term "coding sequence" (CDS) means a nucleotide sequence, which directly specifies the amino acid sequence of its protein product. The boundaries of the coding sequence are generally determined by an open reading frame, which usually begins with the ATG start codon or alternative start codons such as GTG and TTG. The coding sequence may a DNA, cDNA, or recombinant nucleotide sequence Expression Vector The term "expression" includes any step involved in the production of the polypeptide including, but not limited to, transcription, post-transcriptional modification, translation, post-translational modification, and secretion.

The term "expression vector" is defined herein as a linear or circular DNA molecule that comprises a polynucleotide encoding a polypeptide of the invention, and which is operably linked to additional nucleotides that provide for its expression.

A nucleic acid sequence encoding a phytase variant of the invention can be expressed using an expression vector which typically includes control sequences encoding a promoter, operator, ribosome binding site, translation initiation signal, and, optionally, a repressor gene or various activator genes.

The recombinant expression vector carrying the DNA sequence encoding a phytase variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated.

The phytase variant may also be co-expressed together with at least one other enzyme of animal feed interest, such as a phytase, phosphatase, xylanase, galactanase, alpha-galactosidase, protease, phospholipase, amylase, and/or beta-glucanase. The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multi-cistronic), the order in which the genes are cloned may affect the expression levels of the proteins. The phytase variant may also be expressed as a fusion protein, i.e., that the gene encoding the phytase variant has been fused in frame to the gene encoding another protein. This protein may be another enzyme or a functional domain from another enzyme.

Host Cells

The term "host cell", as used herein, includes any cell type which is susceptible to transformation, transfection, transduction, and the like with a nucleic acid construct comprising a polynucleotide of the present invention.

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus,* or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizin, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even more preferred aspect, the yeast host cell is a *Candida, Hansenula, Kluyveromyces, Pichia, Saccharomyces, Schizosaccharomyces,* or *Yarrowia* cell.

In a most preferred aspect, the yeast host cell is a *Pichia pastoris, Pichia methanolica, Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium tri-*

*chothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa*, or *Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* strain cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, Proceedings of the National Academy of Sciences USA 81: 1470-1474. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention relates to methods for producing a phytase variant comprising (a) cultivating a host cell under conditions conducive for production of the phytase; and (b) recovering the phytase.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Transgenic Plants

The present invention also relates to a transgenic plant, plant part, or plant cell which has been transformed with a nucleotide sequence encoding a polypeptide having phytase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, triticale (stabilized hybrid of wheat (*Triticum*) and rye (*Secale*), and maize (corn). Examples of dicot plants are tobacco, legumes, such as sunflower (*Helianthus*), cotton (*Gossypium*), lupins, potato, sugar beet, pea, bean and soybean, and cruciferous plants (family Brassicaceae), such as cauliflower, rape seed, and the closely related model organism *Arabidopsis thaliana*. Low-phytate plants as described in, e.g., U.S. Pat. No. 5,689,054 and are examples of engineered plants.

Examples of plant parts are stem, callus, leaves, root, fruits, seeds, and tubers, as well as the individual tissues comprising these parts, e.g., epidermis, mesophyll, parenchyma, vascular tissues, meristems. Also specific plant cell compartments, such as chloroplast, apoplast, mitochondria, vacuole, peroxisomes, and cytoplasm are considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seed coats.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific cell compartment, tissue or plant part such as seeds or leaves. Regulatory sequences are, for example, described by Tague et al., 1988, Plant Physiology 86: 506.

For constitutive expression, the following promoters may be used: The 35S-CaMV promoter (Franck et al., 1980, Cell 21: 285-294), the maize ubiquitin 1 (Christensen A H, Sharrock R A and Quail 1992. Maize polyubiquitin genes: structure, thermal perturbation of expression and transcript splicing, and promoter activity following transfer to protoplasts by electroporation), or the rice actin 1 promoter (Plant Mo. Biol. 18, 675-689.; Zhang W, McElroy D. and Wu R 1991, Analysis of rice Act1 5' region activity in transgenic rice plants. Plant Cell 3, 1155-1165). Organ-specific promoters may be, for example, a promoter from storage sink tissues such as seeds, potato tubers, and fruits (Edwards & Coruzzi, 1990, Ann. Rev. Genet. 24: 275-303), or from metabolic sink tissues such as meristems (Ito et al., 1994, Plant Mol. Biol. 24: 863-878), a seed specific promoter such as the glutelin, prolamin, globulin, or albumin promoter from rice (Wu et al., 1998, Plant and Cell Physiology 39: 885-889), a *Vicia faba* promoter from the legumin B4 and the unknown seed protein gene from *Vicia faba* (Conrad et al., 1998, Journal of Plant Physiology 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, Plant Physiology 102: 991-1000, the chlorella virus adenine methyltransferase gene promoter (Mitra and Higgins, 1994, Plant Molecular Biology 26: 85-93), or the aldP gene promoter from rice (Kagaya et al., 1995, Molecular and General Genetics 248: 668-674), or a wound inducible promoter such as the potato pin2 promoter (Xu et al., 1993, Plant Molecular Biology 22: 573-588). Likewise, the promoter may be inducible by abiotic treatments such as temperature, drought or modifications in salinity or inducible by exogenously applied substances that activate the promoter, e.g., ethanol, oestrogens, plant hormones like ethylene, abscisic acid, gibberellic acid, and/or heavy metals.

A promoter enhancer element may also be used to achieve higher expression of the polypeptide in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, Science 244: 1293; Potrykus, 1990, Bio/Technology 8: 535; Shimamoto et al., 1989, Nature 338: 274).

Presently, *Agrobacterium tumefaciens*-mediated gene transfer is the method of choice for generating transgenic dicots (for a review, see Hooykas and Schilperoort, 1992, Plant Molecular Biology 19: 15-38), and it can also be used for transforming monocots, although other transformation methods are more often used for these plants. Presently, the method of choice for generating transgenic monocots, supplementing the *Agrobacterium* approach, is particle bombardment (microscopic gold or tungsten particles coated with the transforming DNA) of embryonic calli or developing embryos (Christou, 1992, Plant Journal 2: 275-281; Shimamoto, 1994, Current Opinion Biotechnology 5: 158-162; Vasil et al., 1992, Bio/Technology 10: 667-674). An alternative method for transformation of monocots is based on protoplast transformation as described by Omirulleh et al., 1993, Plant Molecular Biology 21: 415-428.

Following transformation, the transformants having incorporated therein the expression construct are selected and regenerated into whole plants according to methods well-known in the art. Often the transformation procedure is designed for the selective elimination of selection genes either during regeneration or in the following generations by using, e.g., co-transformation with two separate T-DNA constructs or site specific excision of the selection gene by a specific recombinase.

The present invention also relates to methods for producing a polypeptide of the present invention comprising (a) cultivating a transgenic plant or a plant cell comprising a nucleic acid sequence encoding a polypeptide having phytase activity of the present invention under conditions conducive for production of the polypeptide; and (b) recovering the polypeptide.

Compositions and Uses

In still further aspects, the present invention relates to compositions comprising a polypeptide of the present invention, as well as methods of using these.

The polypeptide compositions may be prepared in accordance with methods known in the art and may be in the form of a liquid or a dry composition. For instance, the polypeptide composition may be in the form of granulates or microgranulates. The polypeptide to be included in the composition may be stabilized in accordance with methods known in the art.

The phytase of the invention can be used for degradation, in any industrial context, of, for example, phytate, phytic acid, and/or the mono-, di-, tri-, tetra- and/or penta-phosphates of myo-inositol. It is well known that the phosphate moieties of these compounds chelates divalent and trivalent cations such as metal ions, i.a. the nutritionally essential ions of calcium, iron, zinc and magnesium as well as the trace minerals manganese, copper and molybdenum. Besides, the phytic acid also to a certain extent binds proteins by electrostatic interaction.

Accordingly, preferred uses of the polypeptides of the invention are in animal feed preparations (including human food) or in additives for such preparations.

In a particular embodiment, the polypeptide of the invention can be used for improving the nutritional value of an animal feed. Non-limiting examples of improving the nutritional value of animal feed (including human food), are: Improving feed digestibility; promoting growth of the animal; improving feed utilization; improving bio-availability of proteins; increasing the level of digestible phosphate; improving the release and/or degradation of phytate; improving bio-availability of trace minerals; improving bio-availability of macro minerals; eliminating the need for adding supplemental phosphate, trace minerals, and/or macro minerals; and/or improving egg shell quality. The nutritional value of the feed is therefore increased, and the growth rate and/or weight gain and/or feed conversion (i.e., the weight of ingested feed relative to weight gain) of the animal may be improved.

Furthermore, the polypeptide of the invention can be used for reducing phytate level of manure.

Animals, Animal Feed, and Animal Feed Additives

The term animal includes all animals, including human beings. Examples of animals are non-ruminants, and ruminants. Ruminant animals include, for example, animals such as sheep, goat, and cattle, e.g., cow such as beef cattle and dairy cows. In a particular embodiment, the animal is a non-ruminant animal. Non-ruminant animals include monogastric animals, e.g., pig or swine (including, but not limited to, piglets, growing pigs, and sows); poultry such as turkeys, ducks and chickens (including but not limited to broiler chicks, layers); fish (including but not limited to salmon, trout, tilapia, catfish and carp); and crustaceans (including but not limited to shrimp and prawn).

The term feed or feed composition means any compound, preparation, mixture, or composition suitable for, or intended for intake by an animal.

In the use according to the invention the polypeptide can be fed to the animal before, after, or simultaneously with the diet. The latter is preferred.

In a particular embodiment, the polypeptide, in the form in which it is added to the feed, or when being included in a feed additive, is substantially pure. In a particular embodiment it is well-defined. The term "well-defined" means that the phytase preparation is at least 50% pure as determined by Size-exclusion chromatography (see Example 12 of WO 01/58275). In other particular embodiments the phytase preparation is at least 60, 70, 80, 85, 88, 90, 92, 94, or at least 95% pure as determined by this method.

A substantially pure, and/or well-defined polypeptide preparation is advantageous. For instance, it is much easier to dose correctly to the feed a polypeptide that is essentially free from interfering or contaminating other polypeptides. The term dose correctly refers in particular to the objective of obtaining consistent and constant results, and the capability of optimising dosage based upon the desired effect.

For the use in animal feed, however, the phytase polypeptide of the invention need not be that pure; it may, e.g., include other polypeptides, in which case it could be termed a phytase preparation.

The phytase preparation can be (a) added directly to the feed (or used directly in a treatment process of proteins), or (b) it can be used in the production of one or more intermediate compositions such as feed additives or premixes that is subsequently added to the feed (or used in a treatment process). The degree of purity described above refers to the purity of the original polypeptide preparation, whether used according to (a) or (b) above.

Polypeptide preparations with purities of this order of magnitude are in particular obtainable using recombinant methods of production, whereas they are not so easily obtained and also subject to a much higher batch-to-batch variation when the polypeptide is produced by traditional fermentation methods.

Such polypeptide preparation may of course be mixed with other polypeptides.

The polypeptide can be added to the feed in any form, be it as a relatively pure polypeptide, or in admixture with other components intended for addition to animal feed, i.e., in the form of animal feed additives, such as the so-called premixes for animal feed.

In a further aspect the present invention relates to compositions for use in animal feed, such as animal feed, and animal feed additives, e.g., premixes.

Apart from the polypeptide of the invention, the animal feed additives of the invention contain at least one fat-soluble vitamin, and/or at least one water soluble vitamin, and/or at least one trace mineral. The feed additive may also contain at least one macro mineral.

Further, optional, feed-additive ingredients are colouring agents, e.g., carotenoids such as beta-carotene, astaxanthin, and lutein; aroma compounds; stabilisers; antimicrobial peptides; polyunsaturated fatty acids; reactive oxygen generating species; and/or at least one other polypeptide selected from amongst phytase (EC 3.1.3.8 or 3.1.3.26); phosphatase (EC 3.1.3.1; EC 3.1.3.2; EC 3.1.3.39); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); and/or beta-glucanase (EC 3.2.1.4 or EC 3.2.1.6).

In a particular embodiment these other polypeptides are well-defined (as defined above for phytase preparations).

The phytase of the invention may also be combined with other phytases, for example ascomycete phytases such as *Aspergillus* phytases, for example derived from *Aspergillus ficuum*, *Aspergillus niger*, or *Aspergillus awamori*; or basidiomycete phytases, for example derived from *Peniophora lycii*, *Agrocybe pediades*, *Trametes pubescens*, or *Paxillus involutus*; or derivatives, fragments or variants thereof which have phytase activity.

Thus, in preferred embodiments of the use in animal feed of the invention, and in preferred embodiments of the animal feed additive and the animal feed of the invention, the phytase of the invention is combined with such phytases.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and polypeptides such as an oxidase, an oxygenase or a syntethase.

Usually fat- and water-soluble vitamins, as well as trace minerals form part of a so-called premix intended for addition to the feed, whereas macro minerals are usually separately added to the feed. Either of these composition types, when enriched with a polypeptide of the invention, is an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g., vitamin K3.

Examples of water-soluble vitamins are vitamin B12, biotin and choline, vitamin B1, vitamin B2, vitamin B6, niacin, folic acid and panthothenate, e.g., Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

WO 01/58275 corresponds to U.S. Ser. No. 09/779,334 which is hereby incorporated by reference.

An animal feed composition according to the invention has a crude protein content of 50-800 g/kg, and furthermore comprises at least one polypeptide as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e., Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & Iooijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one protein. The protein may be an animal protein, such as meat and bone meal, and/or fish meal; or it may be a vegetable protein. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g., soybean, lupine, pea, or bean.

In another particular embodiment, the vegetable protein source is material from one or more plants of the family Chenopodiaceae, e.g., beet, sugar beet, spinach or quinoa.

Other examples of vegetable protein sources are rapeseed, sunflower seed, cotton seed, and cabbage.

Soybean is a preferred vegetable protein source.

Other examples of vegetable protein sources are cereals such as barley, wheat, rye, oat, maize (corn), rice, triticale, and sorghum.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

Animal diets can be, e.g., manufactured as mash feed (non pelleted) or pelleted feed. Typically, the milled feed-stuffs are mixed and sufficient amounts of essential vitamins and minerals are added according to the specifications for the species in question. Polypeptides can be added as solid or liquid polypeptide formulations. For example, a solid polypeptide formulation is typically added before or during the mixing step; and a liquid polypeptide preparation is typically added after the pelleting step. The polypeptide may also be incorporated in a feed additive or premix.

The final polypeptide concentration in the diet is within the range of 0.01-200 mg polypeptide protein per kg diet, for example in the range of 5-30 mg polypeptide protein per kg animal diet.

The phytase of the invention should of course be applied in an effective amount, i.e., in an amount adequate for improving solubilisation and/or improving nutritional value of feed. It is at present contemplated that the polypeptide is administered in one or more of the following amounts (dosage ranges): 0.01-200; 0.01-100; 0.5-100; 1-50; 5-100; 10-100; 0.05-50; or 0.10-10—all these ranges being in mg phytase polypeptide protein per kg feed (ppm).

For determining mg phytase polypeptide protein per kg feed, the phytase is purified from the feed composition, and the specific activity of the purified phytase is determined using a relevant assay. The phytase activity of the feed composition as such is also determined using the same assay, and on the basis of these two determinations, the dosage in mg phytase protein per kg feed is calculated.

The same principles apply for determining mg phytase polypeptide protein in feed additives. Of course, if a sample is available of the phytase used for preparing the feed additive or the feed, the specific activity is determined from this sample (no need to purify the phytase from the feed composition or the additive).

Methods for Producing Fermentation Products

Yet another aspect of the present invention relates to the methods for producing a fermentation product, such as, e.g., ethanol, beer, wine, distillers dried grains (DDG), wherein the fermentation is carried out in the presence of a phytase produced by the present invention. Examples of fermentation processes include, for example, the processes described in WO 01/62947. Fermentation is carried out using a fermenting microorganism, such as, yeast.

In a particular embodiment, the present invention provides methods for producing fermentation product, comprising (a) fermenting (using a fermenting microorganism, such as yeast) a carbohydrate containing material (e.g., starch) in the presence of a phytase of the present invention and (b) producing the fermentation product from the fermented carbohydrate containing material.

In a particular embodiment, the present invention provides methods for producing ethanol, comprising fermenting (using a fermenting microorganism, such as yeast) a carbohydrate containing material (e.g., starch) in the presence of a phytase of the present invention and producing or recovering ethanol from the fermented carbohydrate containing material.

In another embodiment, the present invention provides methods for producing ethanol comprising a) hydrolyzing starch, e.g., by a liquefaction and/or saccharification process, a raw starch hydrolysis process, b) fermenting the resulting starch in the presence of a phytase of the present invention, and c) producing ethanol.

The phytase may be added to the fermentation process at any suitable stage and in any suitable composition, including alone or in combination with other enzymes, such as, one or more alpha-amylases, glucoamylases, proteases, and/or cellulases.

In another embodiment, the present invention provides methods for producing ethanol comprising hydrolyzing biomass, and fermenting (using a fermenting microorganism, such as yeast) the resulting biomass in the presence of a phytase of the present invention.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

Chemicals used were commercial products of at least reagent grade.

Example 1

Preparation of Variants, and Determination of Activity

Preparation of Phytase Variants
Expression of Phytase Variants in *Aspergillus oryzae*

The constructs comprising the *C. braakii* phytase variant genes in the examples were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). Also present on the plasmid was the *Aspergillus* selective marker pyrG from *Aspergillus nidulans* enabling growth on minimal media for an *aspergillus* which is pyrG minus. The expression plasmids for phytase variants were transformed into *Aspergillus* as described in Lassen et al., 2001, *Applied and Environmental Micorbiology* 67: 4701-4707. For each of the constructs 4-6 strains were isolated, purified and cultivated in microtiterplates. Expression was determined using a p-nitrophenyl phosphate substrate. The best producing strain was fermented in Shake flasks.

Purification of *C. braakii* Phytase Variants

The fermentation supernatant with the phytase variant was filtered through a Fast PES Bottle top filter with a 0.22 μm cut-off. The resulting solution was diluted with water to the double volume and pH was adjusted to 4.5 with acetic acid. Occasionally, the solution became a little cloudy and this removed by filtration through a Fast PES Bottle top filter with a 0.22 μm cut-off.

After pretreatment the phytase variant was purified by chromatography on S Sepharose, approximately 30 ml in a XK26 column, using as buffer A 50 mM sodium acetate pH 4.5, and as buffer B 50 mM sodium acetate+1 M NaCl pH 4.5. The fractions from the column were analyzed for activity using the phosphatase assay (see below) and fractions with activity were pooled.

In some cases the solution containing the purified phytase variant was concentrated using an Amicon ultra-15 filtering device with a 30 kDa cut-off membrane.

The molecular weight, as estimated from SDS-PAGE, was approximately 45-50 kDa and the purity was >95%.

TABLE 2

Designation of variants

| Extra S-S | Designation | Modifications |
|---|---|---|
| 1 | 10 | K141C/V199C = D |
| 1 | 25 | G52C/S162C = E |
| 1 | 26 | G59C/F100C = G |

TABLE 2-continued

Designation of variants

| Extra S-S | Designation | Modifications |
|---|---|---|
| 1 | 36 | W46C/Q91C = C |
| 1 | 37 | N31C/E176C = F |
| 1 | 38 | N31C/T177C = B |
| 1 | 43 | G52C/A99C = A |
| 1 | 55 | S162C/S247C = H |
| 1 | 61 | N31C/T177C/N203L = B/N203L |
| 1 | 65 | 114-121 (YQKDEEKN -> TQADTSSP)/K141C/E182R/K183Q/T185G/K186L/V199C/S213G/T217A/K336R = Σb/K141C/E182R/K183Q/T185G/K186L/V199C/S213G/T217A/K336R = D/Σb/E182R/K183Q/T185G/K186L/S213G/T217A/K336R = D/ΣKJ |
| 1 | 70 | F66L/114-121 (YQKDEEKN -> TQADTSSP)/K141C/E182R/K183Q/T185G/K186L/T188S/P190T/V199C/S213G/T217A/K336R = Σb/F66L/K141C/E182R/K183Q/T185G/K186L/T188S/P190T/V199C/S213G/T217A/K336R = D/Σb/F66L/E182R/K183Q/T185G/K186L/T188S/P190T/S213G/T217A/K336R = D/ΣKJ/F66L/T188S/P190T |
| 1 | 92 | F66L/R94V/114-121 (YQKDEEKN -> TQADTSS)/K141C/E182K/K183Q/T185G/K186L/T188S/P190T/V199C/P207G/S213G/T217A/K336V = Σd/F66L/R94V/K141C/E182K/K183Q/T185G/K186L/T188S/P190T/V199C/P207G/S213G/T217A/K336V = D/Σd/F66L/R94V/E182K/K183Q/T185G/K186L/T188S/P190T/P207G/S213G/T217A/K336V = D/ΣKU/T188S/P190T/P207G |
| 1 | 97 | F66L/R94V/114-121 (YQKDEEKN -> TQADTSSR)/K141C/T188S/P190T/V199C/P207G//S213G/T217A/K336V = Σa/F66L/R94V/K141C/T188S/P190T/V199C/P207G//S213G/T217A/K336V = D/Σa/F66L/R94V/T188S/P190T/P207G//S213G/T217A/K336V = D/ΣKK |
| 2 | 99 | F66L/R94V/114-121 (YQKDEEKN -> TQADTSSR)/K141C/E182K/K183Q/T185G/K186L/T188S/P190T/V199C/P207G/S213G/T217A/K336V/G52C/A99C = Σa/F66L/R94V/K141C/E182K/K183Q/T185G/K186L/T188S/P190T/V199C/P207G/S213G/T217A/K336V/G52C/A99C = A/D/Σa/F66L/R94V/E182K/K183Q/T185G/K186L/T188S/P190T/P207G/S213G/T217A/K336V = A/D/ΣKK/E182K/K183Q/T185G/K186L |
| 2 | 100 | F66L/R94V/114-121 (YQKDEEKN -> TQADTSSR)/K141C/T188S/P190T/V199C/P207G/S213G/T217A/K336V/G52C/A99C = Σa/F66L/R94V/K141C/T188S/P190T/V199C/P207G/S213G/T217A/K336V/G52C/A99C = A/D/Σa/F66L/R94V/T188S/P190T/P207G/S213G/T217A/K336V = A/D/ΣKK |
| 1 | 110 | G52C/A99C/N203I = A/N203I |
| 1 | 111 | G52C/A99C/N203R = A/N203R |
| 1 | 112 | G52C/A99C/N203K = A/N203K |
| 1 | 113 | G52C/A99C/N203S = A/N203S |
| 1 | 114 | G52C/A99C/N203Q = A/N203Q |
| 1 | 115 | N31C/T177C/N203S = B/N203S |
| 1 | 116 | N31C/T177C/N203T = B/N203T |
| 1 | 117 | N31C/T177C/N203C = B/N203C |
| 1 | 118 | N31C/T177C/N203V = B/N203V |
| 2 | 120 | N31C/G52C/A99C/T177C = A/B |
| 2 | 128 | K24Q/N31C/G52C/A99C/T177C = A/B/K24Q |
| 2 | 130 | K24I/N31C/G52C/A99C/T177C = A/B/K24I |
| 2 | 131 | N31C/G52C/A99C/K129P/T177C = A/B/K129P |
| 2 | 132 | N31C/G52C/A99C/K129Q/T177C = A/B/K129Q |
| 2 | 133 | N31C/G52C/A99C/K129I/T177C = A/B/K129I |
| 3 | 139 | N31C/G52C/A99C/K141C/T177C/V199C = A/B/D |
| 1 | 141 | G52C/A99C/V199C = A/V199C |
| 1 | 142 | G52C/A99C/P190L/V199C = A/P190L/V199C |
| 2 | 143 | G52C/A99C/K141C/V199C = A/D |
| 1 | 144 | G52C/A99C/P207D = A/P207D |
| 1 | 145 | G52C/A99C/N203L = A/N203L |
| 1 | 146 | G52C/A99C/P207G = A/P207G |
| 2 | 147 | N31C/G52C/A99C/T177C/P207G = A/B/P207G |
| 2 | 150 | N31C/G52C/A99C/T177C/N203L/P207G = A/B/N203L/P207G |
| 2 | 151 | K24R/N31C/G52C/A99C/T177C = A/B/K24R |
| 2 | 152 | N31C/G52C/A99C/K129R/T177C = A/B/K129R |
| 2 | 161 | K24R/N31C/G52C/A99C/K129P/T177C = A/B/K24R/K129P |
| 2 | 162 | K24R/N31C/G52C/A99C/K129R/T177C/N203L/P207G = A/B/K24R/K129R/N203L/P207G |
| 2 | 163 | N31C/G52C/A99C/K129R/T177C/N203L/P207G = A/B/K129R/N203L/P207G |
| 2 | 164 | K24R/N31C/G52C/A99C/K129R/T177C/N203L = A/B/K24R/K129R/N203L |
| 2 | 165 | N31C/G52C/A99C/K129R/T177C/N203L = A/B/K129R/N203L |
| 1 | 200 | F66L/R94V/114-121(YQKDEEKN -> TQADTSSR)/K141C/K179N/E182K/K183Q/T185G/K186L/T188S/P190T/V199C/P207G/S213G/T217A/K336V = D/Σa/F66L/R94V/K179N/E182K/K183Q/T185G/K186L/T188S/P190T/P207G/S213G/T217A/K336V = D/ΣKK/K179N/E182K/K183Q/T185G/K186L |

TABLE 2-continued

Designation of variants

| Extra S-S | Designation | Modifications |
|---|---|---|
| 1 | 201 | F66L/R94V/114-121 (YQKDEEKN -> TQADTSSR)/K141C/E182N/K183Q/T185G/K186L/T188S/P190T/V199C/P207G/S213G/T217A/K336V = D/Σa/F66L/R94V/E182K/K183Q/T185G/K186L/T188S/P190T/P207G/S213G/T217A/K336V = D/ΣKK/E182K/K183Q/T185G/K186L |
| 2 | 212 | G52C/R94V/A99C/K116A/E119S/K141C/T188S/P190T/V199C/T217A = A/D/R94V/K116A/E119S/T188S/P190T/T217A |
| 3 | 213 | F66L/R94V/114-121 (YQKDEEKN -> TQADTSSR)/K141C/T188S/P190T/V199C/P207G/S213G/T217A/K336V/G52C/A99C/N31C/T177C = A/B/D/Σa/F66L/R94V/T188S/P190T/P207G/S213G/T217A/K336V = A/B/D/ΣKK |
| 1 | 222 | E1*/E"*/K116A/E119S/K141C/V199C/T217A = D/E1*/E"*/K116A/E119S/T217A |
| 1 | 223 | E1*/E"*/R94V/K116A/E119S/K141C/K186L/T188S/P190T/V199C/T217A = D/E1*/E"*/R94V/K116A/E119S/K186L/T188S/P190T/T217A | wherein A means G52C/A99C, B means N31C/T177C, C means W46C/Q91C, D means K141C/V199C, E means G52C/S162C, F means N31C/E176C, G means G59C/F100C, and H means S162C/S247C; and wherein Σa means the substitution of the fragment TQADTSSR for the fragment YQKDEEKN in positions 114-121, Σb means the substitution of the fragment TQADTSSP for the fragment YQKDEEKN, Σc means the substitution of the fragment TQADTSSN for the fragment YQKDEEKN, Σd means the substitution of the fragment TQADTSS for the fragment YQKDEEKN; and wherein ΣKJ means Σb/E182R/K183Q/T185G/K186L/S213G/T217A/K336R, ΣKU means Σd/F66L/R94V/E182K/K183Q/T185G/K186L/S213G1 T217A/K336V, and ΣKK means Σa/F66L/R94V/T188S/P190T/P207G//S213G/T217A/K336V.

Determination of Phosphatase Activity 75 microliter phytase-containing enzyme solution is dispensed in a microtiter plate well, e. g. NUNC 269620 and 75 microliter substrate is added (for preparing the substrate, two 5 mg p-nitrophenyl phosphate tablets (Sigma, Cat. No. N-9389) are dissolved in 10 ml 0.1 M Na-acetate buffer, pH 5.5). The plate is sealed and incubated 15 min., shaken with 750 rpm at 37° C. After the incubation time 75 microliter stop reagent is added (the stop reagent is 0.1 M di-sodiumtetraborate in water) and the absorbance at 405 nm is measured in a microtiter plate spectrophotometer. One phosphatase unit is defined as the enzyme activity that releases 1 micromol phosphate/min under the given reaction conditions (buffer blind subtracted). The absorbance of 1 micromol p-nitrophenol is determined to be 56 AU (AU=absorbancy units) under assay conditions.

Determination of Phytase Activity 75 microliter phytase-containing enzyme solution, appropriately diluted in 0.25 M sodium acetate, 0.005% (w/v) Tween-20. pH 5.5, is dispensed in a microtiter plate well, e.g., NUNC 269620, and 75 microliter substrate is added (prepared by dissolving 100 mg sodium phytate from rice (Aldrich Cat. No. 274321) in 10 ml 0.25 M sodium acetate buffer, pH 5.5). The plate is sealed and incubated 15 min. shaken with 750 rpm at 37° C. After incubation, 75 microliter stop reagent is added (the stop reagent being prepared by mixing 10 ml molybdate solution (10% (w/v) ammonium hepta-molybdate in 0.25% (w/v) ammonia solution), 10 ml ammonium vanadate (0.24% commercial product from Bie&Berntsen, Cat. No. LAB17650), and 20 ml 21.7% (w/v) nitric acid, and the absorbance at 405 nm is measured in a microtiter plate spectrophotometer. The phytase activity is expressed in the unit of FYT, one FYT being the amount of enzyme that liberates 1 micromole inorganic orthophosphate per minute under the conditions above. An absolute value for the measured phytase activity may be obtained by reference to a standard curve prepared from appropriate dilutions of inorganic phosphate, or by reference to a standard curve made from dilutions of a phytase enzyme preparation with known activity (such standard enzyme preparation with a known activity is available on request from Novozymes N S, Krogshoejvej 36, DK-2880 Bagsvaerd).

Example 2

Specific Activity

The specific activity of a phytase variant is determined on highly purified samples dialysed against 250 mM sodium acetate, pH 5.5. The purity is checked beforehand on an SDS poly acryl amide gel showing the presence of only one component.

The protein concentration is determined by amino acid analysis as follows: An aliquot of the sample is hydrolyzed in 6N HCl, 0.1% phenol for 16 h at 110° C. in an evacuated glass tube. The resulting amino acids are quantified using an Applied Biosystems 420A amino acid analysis system operated according to the manufacturer's instructions. From the amounts of the amino acids the total mass—and thus also the concentration—of protein in the hydrolyzed aliquot can be calculated.

The phytase activity is determined in the units of FYT as described in Example 1 ("Determination of phytase activity"), and the specific activity is calculated as the phytase activity measured in FYT units per mg phytase variant enzyme protein.

Example 3

Screening for Temperature Stability

Strains and Plasmids

E. coli DH12S (available from Gibco BRL) was used for yeast plasmid rescue.

pJCP000 is a S. cerevisiae and E. coli shuttle vector under the control of TPI promoter, constructed from pJC039 described in WO 01/92502, in which the C. braakii phytase gene has been inserted.

*Saccharomyces cerevisiae* YNG318: MATa Dpep4[cir+] ura3-52, leu2-D2, his 4-539 was used for the phytase variants expression. It is described in *J. Biol. Chem.* 272 (15): 9720-9727, 1997.

Media and Substrates

10× Basal solution: Yeast nitrogen base w/o amino acids (DIFCO) 66.8 g/l, succinate 100 g/l, NaOH 60 g/l.

SC-glucose: 20% glucose (i.e., a final concentration of 2%=2 g/100 ml)) 100 ml/1, 5% threonine 4 ml/1, 1% tryptophan 10 ml/1, 20% casamino acids 25 ml/1, 10× basal solution 100 ml/1. The solution is sterilized using a filter of a pore size of 0.20 micrometer. Agar and H₂O (approx. 761 ml) is autoclaved together, and the separately sterilized SC-glucose solution added to the agar solution.

YPD: Bacto peptone 20 g/l, yeast extract 10 g/l, 20% glucose 100 ml/l.

PEG/LiAc solution: 40% PEG4000 50 ml, 5 M Lithium Acetate 1 ml

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, N.Y.; Ausubel, F. M. et al. (eds.) "Current protocols in Molecular Biology", John Wiley and Sons, 1995; Harwood, C. R. and Cutting, S. M. (eds.).

Yeast Transformation

Yeast transformation was carried out by lithium acetate method. Mix 0.5 microL of vector (digested by restriction endonucleases) and 1 microL of PCR fragments. Thaw YNG318 competent cells on ice. Mix 100 microL of the cells, the DNA mixture and 10 microL of carrier DNA (Clontech) in 12 ml polypropylene tubes (Falcon 2059). Add 0.6 ml PEG/LiAc solution and mix gently. Incubate for 30 min at 30° C., and 200 rpm. Incubate for 30 min at 42° C. (heat shock). Transfer to an Eppendorf tube and centrifuge for 5 sec. Remove the supernatant and resolve in 3 ml of YPD. Incubate the cell suspension for 45 min at 200 rpm at 30° C. Pour the suspension to SC-glucose plates and incubate 30° C. for 3 days to make colonies. Yeast total DNA was extracted by the Robzyk and Kassir's method described in *Nucleic Acids Research* 20(14): 3790 (1992).

DNA Sequencing

*E. coli* transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Phytase Expression Vector

The *Citrobacter* phytase gene was amplified with the primer pairs (CbPhyF and CbPhyR). The resulting PCR fragments were introduced into *S. cerevisiae* YNG318 together with the pJC039 vector digested with restriction enzymes to remove the mature part of *Humicola insolens* cutinase gene.

```
CbPhyF (40 mer)
CTCCTGAACTTGTTGCCCGGGAAGAGCAGAACGGAATG

CbPhyR (42 mer)
ATTACATGATGCGGCCCGCGGCCGCCTACTCTGTGACGGCAC
```

The Plasmid, which is termed as pJCP000 from the yeast transformants on SC-glucose plates, was recovered and the internal sequence was determined to confirm the phytase gene.

Construction of Yeast Library and Site-Directed Variants

Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.

General Primers for Amplification and Sequencing

The below primers are used to make DNA fragments containing any mutated fragments by the SOE method together with degenerated primers (AM34+Reverse primer and AM35+forward primer) or just to amplify a whole asparaginase gene (AM34+AM35).

```
AM34    TAGGAGTTTAGTGAACTTGC

AM35    TTCGAGCGTCCCAAAACC
```

| PCR reaction system: | | Conditions: | | |
|---|---|---|---|---|
| 48.5 micro | L H2O | 1 | 94° C. | 2 min |
| 2 beads | puRe Taq Ready-To-Go PCR | 2 | 94° C. | 30 sec |
| Beads (Amersham bioscineces) | | 3 | 55° C. | 30 sec |
| 0.5 micro L X 2 | 100 pmole/micro L | 4 | 72° C. | 90 sec |
| Primers | | 2-4 | 25 cycles | |
| 0.5 micro L | Template DNA | 5 | 72° C. | 10 min |

DNA fragments were recovered from agarose gel by the Qiagen gel extraction Kit. The resulting purified fragments were mixed with the vector digest. The mixed solution was introduced into *Saccharomyces cerevisiae* to construct libraries or site-directed variants by in vivo recombination.

Library Screening (the Primary Membrane Assay)

Yeast libraries were cultivated on SC-glucose plate with a cellulose acetate membrane (upper) and Biodyne C (from Pall gelman) membrane (lower) at 30° C. at least for 3 days. The BiodyneC membranes were transferred to pre-incubated plates containing 20 mM acetate buffer, pH 4.0 and incubated for 1-2 hours at a certain temperature (50° C. in the case of WT as a backbone).

Then, the membranes were removed and soaked in the fresh substrate solution (10 ml 20 mM acetate buffer, pH4.0; 0.01 g, alpha-naphtyl phosphate (sigma); 0.02 g, Fast Garnet GBC (sigma)). Yeast clones corresponding to the positions of red colour developed on the Biodyne C membranes were isolated from cellulose acetate membranes.

Library Screening (the Secondary Relative Activity Selection)

Yeast clones on cellulose acetate membranes were inoculated to a well of a 96-well micro titre plate and cultivated at 28° C. for 3 days. Phytase activity was measured at both 37° C. and the higher temperature (60, 64, 65, 70, 72° C. etc.) to determine the relative activity at a certain temperature. Then the clones with higher relative activity were selected and the sequence was confirmed.

| | |
|---|---|
| Standard, Level control and samples are pipetted into a MTP or 8 strip tube. | 10 µl |
| Pre-heated (50° C.) substrate is added. | 200 µl |
| The 8-stripe tube or MTP is placed in an MTP incubator at 37, 60 and 64° C. (or above). | 30 min. |

-continued

| | |
|---|---|
| Take out 35 μl, add it into 100 μl of stop-complex reagent and mixed 5-20 s. | 35 + 100 μl |
| The sample waits before measurement. | 5-30 min |
| OD is measured at | 750 nm |

Substrate, Sodium Phytate Solution 2.0 mM (Every Time)
Example of preparation of 100 ml:
Sodium phytate 0.1847 g
0.1 M Acetate buffer, pH 4.0 up to 100 ml
Complexing Reagent
Example of preparation of 200 ml:
FeSO4.7H2O 14.64 g
Ammonium heptamolybdate solution up to 200 ml
Stop-Complex Reagent
Example of preparation of 600 ml stop-complex reagent
0.5 M H2SO4 200 ml
Complexing reagent 400 ml
Ammonium heptamolybdate solution
Example of preparation of 1000 ml:
(NH4)6Mo7O24.4H2O 10.0 g
Sulfuric acid 32 ml
Demineralized water up to 1000 ml The results are provided below. The column indicating the relative activity provides first the relative activity of the variant and thereafter the relative activity of the reference phytase used in the determination. The reference is the wild type phytase.

Results

| Variant no. | Modifications (substitutions, insertions or deletions) | Relative activity (100% at 37° C.) |
|---|---|---|
| 65 | D/ΣKJ | 113% at 72° C. (WT19%) |
| 70 | D/ΣKJ/F66L/T188S/P190T | 188% at 72° C. (WT19%) |
| 92 | D/ΣKU/T188S/P190T/P207G | 231% at 72° C. (WT19%) |
| 99 | A/D/ΣKK/E182K/K183Q/T185G/K186L | 277% at 72° C. (WT19%) |
| 100 | A/D/ΣKK | 320% at 72° C. (WT19%) |
| 213 | A/B/D/ΣKK | 147% at 72° C. (WT19%) |

Example 4

Thermostability by DSC

An aliquot of the protein sample of *C. braakii* phytase (purified as described in Example 1) was either, desalted and buffer-changed into 20 mM Na-acetate, pH 4.0 using a prepacked PD-10 column, or dialysed against 2×500 ml 20 mM Na-acetate, pH 4.0 at 4° C. in a 2-3 h step followed by an overnight step. The sample was 0.45 μm filtered and diluted with buffer to approx. 2 A280 units. The dialysis buffer was used as reference in Differential Scanning calorimetry (DSC). The samples were degassed using vacuum suction and stirring for approx. 10 minutes.

A DSC scan was performed on a MicroCal VP-DSC at a constant scan rate of 1.5° C./min from 20-90° C. Data-handling was performed using the MicroCal Origin software (version 4.10), and the denaturation temperature, Td (also called the melting temperature, Tm) is defined as the temperature at the apex of the peak in the thermogram.

The results of DSC for *C. braakii* phytase variants are summarized in the Table 3 below.

TABLE 3

Comparative Thermostability of *C. braakii* Phytases

| Variant | No of S-S | Td 1st Scan (° C.) |
|---|---|---|
| *C. braakii* wt | 0 | 62.0 |
| 10 = D | 1 | 63.8 |
| 36 = C | 1 | 65.4 |
| 38 = B | 1 | 66.8 |
| 43 = A | 1 | 69.6 |
| 115 = B/N203S | 1 | 66.6 |
| 118 = B/N203V | 1 | 64.6 |
| 120 = A/B | 2 | 72.2 |
| 139 = A/B/D | 3 | 74.0 |
| 65 = D/ΣKJ | 1 | 68.3 |
| 70 = D/ΣKJ/F66L/T188S/P190T | 1 | 69.8 |
| 92 = D/ΣKU/T188S/P190T/P207G | 1 | 68.0 |
| 97 = D/ΣKK | 1 | 68.8 |
| 99 = A/D/ΣKK/E182K/K183Q/T185G/K186L | 2 | 76.4 |
| 100 = A/D/ΣKK | 2 | 76.3 |
| 200 = D/ΣKK/K179N/E182K/K183Q/T185G/K186L | 1 | 67.7 |
| 201 = D/ΣKK/E182K/K183Q/T185G/K186L | 1 | 68.4 |
| 212 = A/D/6modifications see Table 2 | 2 | 68.7 |
| 213 = A/B/D/ΣKK | 3 | 79.4 |

Example 5

Temperature Profile

The temperature profile (phytase activity as a function of temperature) was determined for the *C. braakii* phytase and variants in the temperature range of 20-90° C. essentially as described above ("Determination of phytase activity"). However, the enzymatic reactions (100 microliter phytase-containing enzyme solution+100 microliter substrate) were performed in PCR tubes instead of microtiter plates. After a 15 minute reaction period at desired temperature the tubes were cooled to 20° C. for 20 seconds and 150 microliter of each reaction mixture was transferred to a microtiter plate. 75 microliter stop reagent was added and the absorbance at 405 nm was measured in a microtiter plate spectrophotometer. The results are summarized in Table 4 below. The numbers given for each temperature are relative activity (in %) normalized to the value at optimum.

TABLE 4

Relative temperature profiles

| Phytase variant | No of S-S | Temperature (° C.) | | | | | | | | | | | |
|---|---|---|---|---|---|---|---|---|---|---|---|---|---|
| | | 20 | 30 | 40 | 50 | 55 | 60 | 65 | 70 | 75 | 80 | 85 | 90 |
| *C. braakii* wt | 0 | 24 | 40 | 59 | 83 | 95 | 100 | 89 | 25 | 11 | 11 | 9 | 8 |
| 25 | 1 | 23 | 35 | 60 | 83 | 91 | 100 | 90 | 28 | 9 | 11 | 5 | −6 |
| 26 | 1 | 20 | 35 | 54 | 83 | 96 | 100 | 77 | 22 | 7 | 7 | 7 | 4 |
| 36 | 1 | 14 | 28 | 52 | 79 | 99 | 100 | 88 | 59 | 8 | 8 | 7 | 5 |
| 37 | 1 | 19 | 32 | 54 | 79 | 93 | 100 | 89 | 51 | 8 | 8 | 6 | 6 |

TABLE 4-continued

Relative temperature profiles

| Phytase variant | No of S-S | Temperature (° C.) | | | | | | | | | | |
|---|---|---|---|---|---|---|---|---|---|---|---|---|
| | | 20 | 30 | 40 | 50 | 55 | 60 | 65 | 70 | 75 | 80 | 85 | 90 |
| 38 | 1 | 19 | 33 | 53 | 75 | 85 | 100 | 91 | 88 | 17 | 11 | 8 | 5 |
| 43 | 1 | 18 | 30 | 50 | 74 | 85 | 91 | 100 | 97 | 10 | 10 | 9 | 6 |
| 55 | 1 | 17 | 31 | 51 | 71 | 89 | 100 | 99 | 43 | 12 | 9 | 8 | 6 |
| 110 | 1 | 18 | 30 | 48 | 68 | 82 | 94 | 100 | 94 | 27 | 13 | 11 | 9 |
| 115 | 1 | 20 | 33 | 52 | 72 | 82 | 94 | 100 | 89 | 19 | 13 | 10 | 9 |
| 118 | 1 | 20 | 32 | 51 | 71 | 85 | 96 | 100 | 73 | 16 | 12 | 10 | 8 |
| 120 | 2 | 17 | 30 | 50 | 69 | 81 | 93 | 100 | 100 | 87 | 18 | 11 | 9 |
| 139 | 3 | 20 | 33 | 51 | 73 | 86 | 98 | 97 | 100 | 80 | 63 | 10 | 5 |
| 165 | 2 | 18 | 26 | 37 | 57 | 73 | | 100 | 84 | 78 | 14 | 9 | 6 |
| 222 | 1 | 25 | 42 | 55 | 75 | | 100 | 86 | 53 | 13 | 10 | 9 | 9 |
| 223 | 1 | 20 | 38 | 49 | 73 | | 100 | 85 | 27 | 9 | 8 | 5 | 5 |
| 10 | 1 | 22 | 35 | 53 | 77 | 86 | 98 | 100 | 45 | | 10 | | 8 |
| 65 | 1 | 26 | 38 | 55 | 77 | 95 | 100 | 91 | 34 | 12 | 9 | 4 | 2 |
| 70 | 1 | 23 | 36 | 56 | 76 | 85 | 100 | 87 | 88 | 60 | 15 | 12 | 8 |
| 92 | 1 | 18 | 30 | 49 | 67 | 81 | 94 | 100 | 98 | 74 | 16 | 12 | 10 |
| 97 | 1 | 18 | 30 | 48 | 67 | 83 | 95 | 100 | 96 | 68 | 15 | 11 | 9 |
| 99 | 2 | 19 | 33 | 46 | 73 | 85 | 92 | 91 | 100 | 97 | 82 | 15 | 10 |
| 100 | 2 | 20 | 32 | 52 | 74 | 84 | 93 | 89 | 100 | 96 | 82 | 15 | 11 |
| 200 | 1 | 17 | 30 | 50 | 73 | 81 | 88 | 96 | 100 | 50 | 13 | 7 | 4 |
| 201 | 1 | 16 | 31 | 48 | 71 | 80 | 87 | 96 | 100 | 60 | 13 | 7 | 4 |
| 212 | 2 | 18 | 30 | 48 | 67 | 77 | 100 | 92 | 97 | 59 | 12 | 6 | 6 |
| 213 | 3 | 15 | 28 | 44 | 55 | 76 | 97 | 91 | 97 | 100 | 88 | 27 | 2 |

Example 6 pH Profile

The pH profile was determined at 37° C. in the pH range of 2.0 to 7.5 (in 0.5 pH-unit steps) as described above in the section "Determination of phytase activity", except that a buffer cocktail (50 mM glycine, 50 mM acetic acid and 50 mM Bis-Tris was used instead of the 0.25 M sodium acetate pH 5.5 buffer. The results are summarized in table 5 below. The values given for each pH in the range of 2.0-7.5 are the relative activity in % normalized to the value at optimum.

TABLE 5

Relative pH profiles at 37° C.

| Variant | pH | | | | | | | | | | | |
|---|---|---|---|---|---|---|---|---|---|---|---|---|
| | 2 | 2.5 | 3 | 3.5 | 4 | 4.5 | 5 | 5.5 | 6 | 6.5 | 7 | 7.5 |
| C. braakii wt | 30 | 59 | 88 | 100 | 99 | 92 | 80 | 64 | 33 | 13 | 0 | −1 |
| 26 | 30 | 56 | 83 | 99 | 100 | 92 | 76 | 59 | 40 | 18 | 4 | 1 |
| 36 | −9 | 9 | 39 | 73 | 94 | 100 | 82 | 57 | 23 | −6 | −7 | −7 |
| 37 | 35 | 59 | 87 | 98 | 100 | 94 | 80 | 57 | 35 | 10 | 0 | −1 |
| 38 | 31 | 61 | 86 | 100 | 100 | 91 | 74 | 58 | 32 | 8 | 1 | 0 |
| 43 | 26 | 60 | 81 | 92 | 100 | 91 | 78 | 58 | 39 | 17 | 3 | −1 |
| 55 | 26 | 52 | 80 | 94 | 98 | 100 | 90 | 66 | 42 | 13 | −1 | 1 |
| 110 | 32 | 61 | 89 | 95 | 100 | 95 | 82 | 60 | 35 | 13 | 2 | 0 |
| 115 | 50 | 74 | 95 | 100 | 100 | 100 | 97 | 75 | 52 | 20 | 2 | 0 |
| 118 | 28 | 63 | 87 | 97 | 100 | 94 | 83 | 54 | 33 | 9 | −1 | −1 |
| 120 | 30 | 52 | 83 | 96 | 100 | 90 | 83 | 59 | 34 | 13 | 0 | −2 |
| 139 | 26 | 56 | 82 | 95 | 100 | 91 | 83 | 60 | 33 | 12 | 1 | 0 |
| 143 | 30 | 59 | 85 | 96 | 100 | 95 | 81 | 61 | 36 | 13 | −1 | 1 |
| 165 | 35 | 55 | 84 | 94 | 100 | 91 | 83 | 61 | 49 | 24 | 7 | 1 |
| 222 | 22 | 49 | 81 | 100 | 100 | 96 | 80 | 60 | 35 | 12 | 1 | −2 |
| 223 | 17 | 46 | 76 | 95 | 100 | 91 | 80 | 59 | 38 | 17 | 3 | 0 |
| 10 | 26 | 59 | 86 | 100 | 100 | 94 | 74 | 58 | 35 | 16 | 3 | 0 |
| 65 | 26 | 45 | 78 | 99 | 100 | 83 | 72 | 51 | 30 | 10 | −1 | 0 |
| 70 | 25 | 47 | 75 | 86 | 100 | 80 | 67 | 51 | 29 | 9 | 1 | 1 |
| 92 | 34 | 66 | 92 | 100 | 99 | 89 | 65 | 37 | 19 | 6 | 0 | 0 |
| 97 | 37 | 65 | 90 | 100 | 91 | 88 | 67 | 41 | 19 | 7 | 0 | 0 |
| 99 | 39 | 62 | 96 | 95 | 100 | 86 | 63 | 37 | 18 | 5 | −1 | 0 |
| 100 | 41 | 64 | 96 | 95 | 100 | 88 | 66 | 37 | 19 | 6 | 1 | 0 |
| 200 | 37 | 62 | 96 | 95 | 100 | 88 | 66 | 40 | 19 | 6 | 1 | 0 |
| 201 | 37 | 61 | 89 | 100 | 97 | 88 | 65 | 39 | 19 | 6 | 1 | 0 |
| 212 | 26 | 59 | 81 | 96 | 100 | 93 | 74 | 58 | 36 | 8 | 0 | 0 |
| 213 | 46 | 75 | 87 | 100 | 93 | 80 | 55 | 33 | 15 | 3 | −2 | −1 |

Example 7

Steam Stability

Method 1

Residual activity of phytase molecules after steam treatment was evaluated using the following assay:

20 μL of each purified enzyme sample is dispensed into a single well of a Corning® 96 Well (1×8 Stripwell™) plate (Corning, Lowell, Mass., USA) and subsequently evaporated to dryness in a vacuum centrifuge (Genevac EZ-1 Plus, Genevac Ltd, Suffolk, UK). The steam incubation is performed in a closed styropor container with the inner dimensions 27×18×20 cm. The samples, in open strips, are placed approximately 10 cm above the bottom of the container on a metal rack, in order not to be in contact with the water.

One liter of boiling water is poured into the container, the lid is closed and the temperature of the produced steam monitored using a thermometer mounted in the lid of the container. The incubation proceeds for 90 seconds from the moment the water is poured into the container. During this period the temperature increases to about 85° C. Immediately after the incubation the samples are cooled down on ice, re-suspended and evaluated with respect to phytase activity using the colorimetric p-nitrophenyl phosphate (pNPP) assay (Sigma, Broendby, DK). Each enzyme sample is compared to a similar sample that had not been steam treated in order to calculate residual activity.

The results are presented in Tables 6 and 7 below.

TABLE 6

Steam Stability determined by method 1. Two or three numbers represent data from two or three different wells.

| Variant | No of S-S | Residual Activity [%] |
|---|---|---|
| C. braakii wt | 0 | 6; 11 |
| 10 = D | 1 | 9 |
| 38 = B | 1 | 13 |
| 43 = A | 1 | 26; 64 |
| 120 = A/B | 2 | 57; 70; 66 |
| 139 = A/B/D | 3 | 66 |
| 100 = A/D/ΣKK | 2 | 88; 77 |
| 212 = A/D/6modifications | 2 | 59 |
| 213 = A/B/D/ΣKK | 3 | 107; 66 |

Method 2

In these experiments a modified set-up was used whereby the steam is provided from a steam generator and led into the box. The samples placed on a plate are inserted into the box through a drawer when the temperature has reached. Upon the insertion of the samples the temperature drops 4° C. Incubation is performed for 60 seconds while the temperature remains approximately constant at 90° C. Thereafter the plate is quickly removed from the box and the samples placed on ice. The samples are analyzed as in method 1.

TABLE 7

Steam Stability determined by method 2. Two or three numbers represent data from two or three different wells.

| Variant | No of S-S | Residual Activity [%] |
|---|---|---|
| C. braakii wt | 0 | 4; 5 |
| 10 = D | 1 | 10 |
| 38 = B | 1 | 13 |
| 43 = A | 1 | 18; 16 |
| 120 = A/B | 2 | 25; 50; 28 |
| 139 = A/B/D | 3 | 35 |
| 100 = A/D/ΣKK | 2 | 79; 56 |
| 212 = A/D/6modifications | 2 | 31 |
| 213 = A/B/D/ΣKK | 3 | 38; 45 |

In the Tables above the variants are as provided in Table 2.

Example 8

Pelleting Stability Tests

Measurements of Pelleting Stability

Approximately 50 g enzyme granulate was pre-mixed with 10 kg feed for 10 minutes in a small horizontal mixer. This premix was mixed with 90 kg feed for 10 minutes in a larger horizontal mixer. From the mixer the feed was led to the conditioner (a cascade mixer with steam injection) at a rate of approximately 300 kg/hour. The conditioner heated up the feed to 95° C. (measured at the outlet) by injecting steam. The residence time in the conditioner was 30 seconds. From the conditioner the feed was led to a Simon Heesen press equipped with 3.0×35 mm horizontal die and pressed to pellets with a length of around 15 mm. After the press the pellets were placed in an air cooler and cooled for 15 minutes.

Feed Formulation:
- 74.0% Grind corn
- 5.0% soy oil
- 20.7% Toasted soy grits
- 0.3% Solivit Mikro 106 premix of minerals and vitamins
- 12% water content Test 1

A powder consisting of:
- 1.50 kg fibrous cellulose, Arbocel BC200
- 0.75 kg carbohydrate binder, Avedex W80
- 11.50 kg finely ground sodium sulphate is granulated in a Lödige mixer FM 50 with a granulation liquid consisting of:
- 0.75 kg carbohydrate binder, Avedex W80
- 2.60 kg phytase C. braakii wt concentrate
- 0.45 kg water The granulation is performed in a manner as described in U.S. Pat. No. 4,106,991, Example 1. The obtained granulate is dried in a fluid bed to a water content below 1% and sifted to obtain a product with the particle range 250 μm to 850 μm. Finally, the product is coated with 9.5% palm oil and 23.5% calcium carbonate in a manner as described in U.S. Pat. No. 4,106,991, Example 22.

Test 2

A powder consisting of:
- 1.6 kg fibrous cellulose, Arbocel BC200
- 0.80 kg carbohydrate binder, Avedex W80
- 12.16 kg finely ground sodium sulphate is granulated in a Lödige mixer FM 50 with a granulation liquid consisting of:
- 0.80 kg carbohydrate binder, Avedex W80
- 2.71 kg phytase variant 100 concentrate
- 0.8 kg water The granulation is performed in a manner as described in U.S. Pat. No. 4,106,991, Example 1. The obtained granulate is dried in a fluid bed to a water content below 1% and sifted to obtain a product with the particle range 250 μm to 850 μm. Finally, the product is coated with 8.5% palm oil and 22% calcium carbonate in a manner as described in U.S. Pat. No. 4,106,991, Example 22.

Test 3

A powder consisting of:
1.6 kg fibrous cellulose, Arbocel BC200
0.80 kg carbohydrate binder, Avedex W80
12.01 kg finely ground sodium sulphate
is granulated in a Lödige mixer FM 50 with a granulation liquid consisting of:
0.80 kg carbohydrate binder, Avedex W80
3.50 kg phytase variant 213 concentrate
0.05 kg water The granulation is performed in a manner as described in U.S. Pat. No. 4,106,991, Example 1. The obtained granulate is dried in a fluid bed to a water content below 1% and sifted to obtain a product with the particle range 250 μm to 850 μm. Finally, the product is coated with 8% palm oil and 22% calcium carbonate in a manner as described in U.S. Pat. No. 4,106,991, Example 22.

The samples produced in Test 1 to Test 3 were tested in a pelleting trial at 95° C., outlet of the conditioner. The phytase content was measured using analytical method EB-SM 0559.02 version 01 (available from Novozymes upon request) prior to pelletizing and in the feed pellets after pelletizing. The following residual activities of the phytase were found:

TABLE 8

Pelleting Stability

| Test | Variant | No of S-S | Residual activity of the Phytase in [%] |
|---|---|---|---|
| 1 | C.B. wt | 0 | 14 |
| 2 | 100 = A/D/ΣKK | 2 | 58 |
| 3 | 213 = A/B/D/ΣKK | 3 | 57 |

The conclusion is that the variants have improved the pelleting stability compared to the reference Test 1.

In the Table above the variants are as provided in Table 2.

Example 9

Performance in Animal Feed in an In Vitro Model

The performance in animal feed of a number of phytase variants of the invention are compared in an in vitro model to the performance of a reference protein such as SEQ ID NO:2. The in vitro model simulates gastro-intestinal conditions in a monogastric animal and correlates well with results obtained in animal trials in vivo. The version used in this example simulates the crop and stomach of a broiler. The comparison is performed as follows:

Phytase activity in the variant sample is determined as described in Example 1 under "Determination of phytase activity".

Feed pellets from a broiler feeding trial—and with maize, soybean meal and soybean oil as main constituents—are pre-incubated at 40° C. and pH 4.6 for 5 minutes followed by the addition of suitable dosages of the phytases (identical dosages are used for all phytases to be tested to allow comparison), for example between 125 to 1000 phytase units FYT/kg feed, or buffer in the control samples. After 5 minutes of incubation, pepsin (3000 U/g feed) in an HCl-solution is added and in this way pH is reduced to 3. The samples are then incubated at 40° C. for another 5 minutes.

The reactions are stopped and phytic acid and inositol-phosphates extracted by addition of HCl to a final concentration of 0.5 M and incubation at 40° C. for 2 hours, followed by one freeze-thaw cycle and 1 hour incubation at 40° C.

Phytic acid and inositol-phosphates are separated by high performance ion chromatography as described by Chen et al., 2003, *Journal of Chromatography A* 1018: 41-52 and quantified as described by Skoglund et al., 1997, *J. Agric. Food Chem.* 45: 431-436.

Degradation of phytate is then calculated as the difference in inositol-6-phosphate bound phosphorous (IP6-P) between phytase-treated and non-treated samples. The relative performance of the variant is calculated as the percentage of phytate degradation by the wild type phytase.

The relative degradation of the phytase variants (Table 9) show that the variants are all capable of degrading inositol-6-phosphate in the in vitro system applied. Certain candidates performed better than the wild type (e.g., variant: 38, variant: 99, variant: 100 and variant: 213) whereas others were not as efficient in vitro as the wild type (e.g., variant: 120).

TABLE 11

In vitro degradation of IP6-P from a soybean/maize based diet. Phytate degradation of the variant is calculated as the percentage of phytate degradation by the wild type phytase.

| Phytase variant | Phytase dosage (FYT/kg feed) | Phytate degradation of the variant as percentage of phytate degradation by the wild type (several numbers represent data from different trials) |
|---|---|---|
| 38 = B | 125 | 167 |
| As above | 250 | 100 |
| As above | 500 | 114 |
| As above | 1000 | 109 |
| 120 = A/B | 500 | 67 |
| As above | 1000 | 85 |
| 99 = A/D/ΣKK/E182K/K183Q/T185G/K186L | 500 | 194; 188 |
| As above | 1000 | 133; 127 |
| 100 = A/D/ΣKK | 125 | 84; 198 |
| As above | 250 | 238 |
| As above | 500 | 170; 180; 180 |
| As above | 1000 | 132; 125 |
| 213 = A/B/D/ΣKK | 125 | 189 |
| As above | 250 | 256 |

In the Table above the variants are as provided in Table 2.

Example 10

Performance in an In Vivo Pig Trial

Comparative evaluation of the effects of graded amounts of the *C. braakii* wild type phytase and a variant on the faecal digestibility and excretion of phosphorus and calcium in growing pigs.

Sixty four Large White×Landrace pigs having an initial body weight of 43.55±4.35 kg were used.

The animals were housed in floor-pen cages in an environmentally controlled room. Each pen had a plastic-coated welded wire floor and was equipped with two water nipples and four stainless-steel individualized feeders. Room temperature was 21-22° C. and humidity percentage was 50%.

The pigs were fed a basal diet formulated to provide phosphorus (P) exclusively from vegetable origin during an adaptive period of 14 days. After that period they were allocated into 16 equal groups of 4 animals each.

They were fed for 12 days the basal diet or this diet supplemented with 1000 or 2000 U/kg of C. braakii wild type phytase or with 500, 1000 or 2000 U/kg of the variant designated 100 having 2 additional disulfide bonds.

An indigestible tracer (chromium oxide) was added at a concentration of 0.4% to all the diets allowing calculation of the digestibility of P and calcium (Ca). The feed was distributed ad libitum in mash form, under pen feed consumption control, and the animals had free access to drinking water. The digestibility of Ca was not corrected for Ca intake with the drinking water.

Faecal P, Ca and Cr concentrations were measured at the $12^{th}$ day of the second period. Faeces were sampled individually, in approximately the same amount at the same time of the day, during the last 3 days preceding that date. Thus, for each dietary treatment and for each criterion a total of 12 individual determinations have been performed. All minerals were determined according to standard Association of Official Analytical Chemists (1990) methods using a Vista-MPX ICP-OES spectrometer. The apparent digestibility (% of the intake) of the minerals was calculated for the mentioned 3 day period.

The mean P faecal concentration of the enzyme supplemented animals was very significantly lower than that observed for the animals ingesting the control diet (a).

The P digestibility was dose depend and highly significantly improved with the two phytases in all supplemented groups (b). The highest P digestibility was observed in the variant 100 supplemented group at 2000 U/kg.

The faecal excretion of P was significantly reduced in all the phytase supplemented animals and for all the tested inclusion levels (c).

The highest apparent absorbed P was observed in the variant 100 supplemented group at 2000 U/kg (d).

The P equivalences, considered as supplemental P digested comparatively to the non-supplemented control, were highly significantly greater to the control in all phytase supplemented diets (e).

The Ca digestibility was improved with the tested enzymes and at all inclusion levels (f).

The results are presented in the following Table 12

TABLE 12

Residual levels of parameters for digestibility

| | Dose (U/kg) | | | |
|---|---|---|---|---|
| | 0 | 500 | 1000 | 2000 |
| (a) Phosphorus fecal concentration (mg/g DM) | | | | |
| Wt | | | 14.6 | 12.2 |
| Variant 100 = A/D/ΣKK | | 13.5 | 12.0 | 12.0 |
| Control | 18.3 | | | |
| (b) Phosphorus apparent fecal digestibility (%) | | | | |
| Wt | | | 48.8 | 49.8 |
| Variant 100 = A/D/ΣKK | | 42.5 | 54.0 | 55.2 |
| Control | 27.9 | | | |
| (c) Phosphorus excretion (mg/g DM) | | | | |
| Wt | | | 1.94 | 1.95 |
| Variant 100 = A/D/ΣKK | | 2.17 | 1.72 | 1.73 |
| Control | 2.80 | | | |
| (d) Phosphorus absorption (mg/g) | | | | |
| Wt | | | 1.85 | 1.94 |
| Variant 100 = A/D/ΣKK | | 1.60 | 2.02 | 2.12 |
| Control | 1.09 | | | |
| (e) Phosphorus equvalences (mg/g) | | | | |
| Wt | | | 0.76 | 0.84 |
| Variant 100 = A/D/ΣKK | | 0.52 | 0.94 | 1.04 |
| Control | 0.00 | | | |
| (f) Calcium apparent digestibility (%) | | | | |
| Wt | | | 57.5 | 60.9 |
| Variant 100 = A/D/ΣKK | | 59.9 | 59.5 | 58.5 |
| Control | 51.0 | | | |

Example 11

Calculating Percentage of Identity and Identifying Corresponding Positions

SEQ ID NO:9 was aligned with SEQ ID NO:2 using the Needle program from the EMBOSS package version 2.8.0. The substitution matrix used was BLOSUM62, the gap opening penalty was 10.0, and the gap extension penalty was 0.5.

The resulting alignment is shown in FIG. 1.

The degree of identity between SEQ ID NO:9 and SEQ ID NO:2 is calculated as follows: The number of exact matches is 406 (all those with a vertical stroke). The length of the shortest sequence is 411 (SEQ ID NO:2). The percentage of identity is 406/411×100%=98.8%.

The alignment of FIG. 1 is also used for deriving corresponding positions as follows: Amino acids on top of each other in this alignment are in corresponding positions. For example, amino acid Q in position 3 of SEQ ID NO:2 corresponds to amino acid P in position 25 of SEQ ID NO:9. For the present purposes we refer to the position number of SEQ ID NO:2. Therefore, SEQ ID NO:9 may be considered a variant of SEQ ID NO:2 which comprises the substitution Q3P.

Other differences in the form of substitutions within the overlap of the alignment are found in positions 31, 121, 132, and 139, viz. N31D, N121T, K132T, and Q139K.

Additional differences are found in the N-terminus, where SEQ ID NO:9 has an extension of 22 amino acids as compared to SEQ ID NO:2.

Overall, SEQ ID NO:9 may therefore be considered the following variant of SEQ ID NO:2: *0aM/*0bS/*0cT/*0dF/*0eI/*0fI/*0gR/*0hL/*0iL/*0jF/*0kF/*0mS/*0nL/*0oL/*0pC/*0qG/*0rS/*0sF/*0tS/*0uI/*0vH/*0wA/Q3P/N31D/N121T/K132T/Q139K.

The invention claimed is:

1. A variant phytase having at least 90% sequence identity to SEQ ID NO:2 and comprising a disulfide bridge between positions 31/177 and a disulfide bridge between positions 52/99.

2. The variant phytase of claim 1, which further comprises a disulfide bridge between positions 141/199.

3. The variant phytase of claim 1, which further comprises a substitution of TQADTSSR at positions 114-121 with YQKDEEKN and the substitutions F66L/R94V/T188S/P190T/P207G/S213G/T217A/K336V.

4. The variant phytase of claim 2, which further comprises a substitution of TQADTSSR at positions 114-121 with YQKDEEKN and the substitutions F66L/R94V/T188S/P190T/P207G/S213G/T217A/K336V.

5. The variant phytase of claim 1, which has at least 95% sequence identity to SEQ ID NO:2.

6. The variant phytase of claim 1, which has at least 97% sequence identity to SEQ ID NO:2.

7. The variant phytase of claim 2, which has at least 95% sequence identity to SEQ ID NO:2.

8. The variant phytase of claim 2, which has at least 97% sequence identity to SEQ ID NO:2.

9. The variant phytase of claim 3, which has at least 95% sequence identity to SEQ ID NO:2.

10. The variant phytase of claim 4, which has at least 95% sequence identity to SEQ ID NO:2.

11. A composition comprising the phytase variant of claim 1, and
    (a) at least one fat soluble vitamin;
    (b) at least one water soluble vitamin; and/or
    (c) at least one trace mineral.

12. A composition comprising the phytase variant of claim 2, and
    (a) at least one fat soluble vitamin;
    (b) at least one water soluble vitamin; and/or
    (c) at least one trace mineral.

13. A composition comprising the phytase variant of claim 3, and
    (a) at least one fat soluble vitamin;
    (b) at least one water soluble vitamin; and/or
    (c) at least one trace mineral.

14. A composition comprising the phytase variant of claim 4, and
    (a) at least one fat soluble vitamin;
    (b) at least one water soluble vitamin; and/or
    (c) at least one trace mineral.

15. A process for reducing phytate levels in animal manure comprising feeding an animal with an effective amount of the composition of claim 11.

16. A process for reducing phytate levels in animal manure comprising feeding an animal with an effective amount of the composition of claim 12.

17. A process for reducing phytate levels in animal manure comprising feeding an animal with an effective amount of the composition of claim 13.

18. A process for reducing phytate levels in animal manure comprising feeding an animal with an effective amount of the composition of claim 14.

19. A method for producing a fermentation product, comprising (a) fermenting using a fermenting microorganism a carbohydrate containing material in the presence of the phytase variant of claim 1 and (b) producing the fermentation product or fermentation coproduct from the fermented carbohydrate containing material.

20. A method for producing a fermentation product, comprising (a) fermenting using a fermenting microorganism a carbohydrate containing material in the presence of the phytase variant of claim 2 and (b) producing the fermentation product or fermentation coproduct from the fermented carbohydrate containing material.

21. A method for producing a fermentation product, comprising (a) fermenting using a fermenting microorganism a carbohydrate containing material in the presence of the phytase variant of claim 3 and (b) producing the fermentation product or fermentation coproduct from the fermented carbohydrate containing material.

22. A method for producing a fermentation product, comprising (a) fermenting using a fermenting microorganism a carbohydrate containing material in the presence of the phytase variant of claim 4 and (b) producing the fermentation product or fermentation coproduct from the fermented carbohydrate containing material.

23. The method of claim 19, wherein the fermentation product is ethanol, beer, wine, or distillers dried grains (DDG).

24. The method of claim 20, wherein the fermentation product is ethanol, beer, wine, or distillers dried grains (DDG).

\* \* \* \* \*

SEQUENCE LISTING

<160> NUMBER OF SEQ ID NOS: 9

<210> SEQ ID NO 1
<211> LENGTH: 1233
<212> TYPE: DNA
<213> ORGANISM: Citrobacter braakii
<220> FEATURE:
<221> NAME/KEY: mat_peptide
<222> LOCATION: (1)..(1233)
<220> FEATURE:
<221> NAME/KEY: CDS
<222> LOCATION: (1)..(1233)

<400> SEQUENCE: 1

| | | | | | | | | | | | | | | | | |
|---|---|---|---|---|---|---|---|---|---|---|---|---|---|---|---|---|
| gaa | gag | cag | aat | ggt | atg | aaa | ctt | gag | cgg | gtt | gtg | ata | gtg | agt | cgt | 48 |
| Glu | Glu | Gln | Asn | Gly | Met | Lys | Leu | Glu | Arg | Val | Val | Ile | Val | Ser | Arg | |
| 1 | | | | 5 | | | | | 10 | | | | | 15 | | |
| cat | gga | gta | aga | gca | cct | acg | aag | ttc | act | cca | ata | atg | aaa | aat | gtc | 96 |
| His | Gly | Val | Arg | Ala | Pro | Thr | Lys | Phe | Thr | Pro | Ile | Met | Lys | Asn | Val | |
| | | | 20 | | | | | 25 | | | | | 30 | | | |
| aca | ccc | gat | caa | tgg | cca | caa | tgg | gat | gtg | ccg | tta | gga | tgg | cta | acg | 144 |
| Thr | Pro | Asp | Gln | Trp | Pro | Gln | Trp | Asp | Val | Pro | Leu | Gly | Trp | Leu | Thr | |
| | | | 35 | | | | | 40 | | | | | 45 | | | |
| cct | cgt | ggg | gga | gaa | ctt | gtt | tct | gaa | tta | ggt | cag | tat | caa | cgt | tta | 192 |
| Pro | Arg | Gly | Gly | Glu | Leu | Val | Ser | Glu | Leu | Gly | Gln | Tyr | Gln | Arg | Leu | |
| | 50 | | | | | 55 | | | | | 60 | | | | | |
| tgg | ttc | acg | agc | aaa | ggt | ctg | ttg | aat | aat | caa | acg | tgc | cca | tct | cca | 240 |
| Trp | Phe | Thr | Ser | Lys | Gly | Leu | Leu | Asn | Asn | Gln | Thr | Cys | Pro | Ser | Pro | |
| 65 | | | | | 70 | | | | | 75 | | | | | 80 | |
| ggg | cag | gtt | gct | gtt | att | gca | gac | acg | gat | caa | cgc | acc | cgt | aaa | acg | 288 |
| Gly | Gln | Val | Ala | Val | Ile | Ala | Asp | Thr | Asp | Gln | Arg | Thr | Arg | Lys | Thr | |
| | | | | 85 | | | | | 90 | | | | | 95 | | |
| ggt | gag | gcg | ttt | ctg | gct | ggg | tta | gca | cca | aaa | tgt | caa | att | caa | gtg | 336 |
| Gly | Glu | Ala | Phe | Leu | Ala | Gly | Leu | Ala | Pro | Lys | Cys | Gln | Ile | Gln | Val | |
| | | | | 100 | | | | | 105 | | | | | 110 | | |
| cat | tat | cag | aag | gat | gaa | gaa | aaa | aat | gat | cct | ctt | ttt | aat | ccg | gta | 384 |
| His | Tyr | Gln | Lys | Asp | Glu | Glu | Lys | Asn | Asp | Pro | Leu | Phe | Asn | Pro | Val | |
| | | | 115 | | | | | 120 | | | | | 125 | | | |
| aaa | atg | ggg | aaa | tgt | tcg | ttt | aac | aca | ttg | cag | gtt | aaa | aac | gct | att | 432 |
| Lys | Met | Gly | Lys | Cys | Ser | Phe | Asn | Thr | Leu | Gln | Val | Lys | Asn | Ala | Ile | |
| | 130 | | | | | 135 | | | | | 140 | | | | | |
| ctg | gaa | cgg | gcc | gga | gga | aat | att | gaa | ctg | tat | acc | caa | cgc | tat | caa | 480 |
| Leu | Glu | Arg | Ala | Gly | Gly | Asn | Ile | Glu | Leu | Tyr | Thr | Gln | Arg | Tyr | Gln | |
| 145 | | | | | 150 | | | | | 155 | | | | | 160 | |
| tct | tca | ttt | cgg | acc | ctg | gaa | aat | gtt | tta | aat | ttc | tca | caa | tcg | gag | 528 |
| Ser | Ser | Phe | Arg | Thr | Leu | Glu | Asn | Val | Leu | Asn | Phe | Ser | Gln | Ser | Glu | |
| | | | | 165 | | | | | 170 | | | | | 175 | | |
| aca | tgt | aag | act | aca | gaa | aag | tct | acg | aaa | tgc | aca | tta | cca | gag | gct | 576 |
| Thr | Cys | Lys | Thr | Thr | Glu | Lys | Ser | Thr | Lys | Cys | Thr | Leu | Pro | Glu | Ala | |
| | | | 180 | | | | | 185 | | | | | 190 | | | |
| tta | ccg | tct | gaa | ctt | aag | gta | act | cct | gac | aat | gta | tca | tta | cct | ggt | 624 |
| Leu | Pro | Ser | Glu | Leu | Lys | Val | Thr | Pro | Asp | Asn | Val | Ser | Leu | Pro | Gly | |
| | | 195 | | | | | 200 | | | | | 205 | | | | |
| gcc | tgg | agt | ctt | tct | tcc | acg | ctg | act | gag | ata | ttt | ctg | tta | caa | gag | 672 |
| Ala | Trp | Ser | Leu | Ser | Ser | Thr | Leu | Thr | Glu | Ile | Phe | Leu | Leu | Gln | Glu | |
| | 210 | | | | | 215 | | | | | 220 | | | | | |
| gcc | cag | gga | atg | cca | cag | gta | gcc | tgg | ggg | cgt | att | acg | gga | gaa | aaa | 720 |
| Ala | Gln | Gly | Met | Pro | Gln | Val | Ala | Trp | Gly | Arg | Ile | Thr | Gly | Glu | Lys | |
| 225 | | | | | 230 | | | | | 235 | | | | | 240 | |
| gaa | tgg | aga | gat | ttg | tta | agt | ctg | cat | aac | gct | cag | ttt | gat | ctt | ttg | 768 |
| Glu | Trp | Arg | Asp | Leu | Leu | Ser | Leu | His | Asn | Ala | Gln | Phe | Asp | Leu | Leu | |
| | | | | 245 | | | | | 250 | | | | | 255 | | |

```
caa aga act cca gaa gtt gcc cgt agt agg gcc aca cca tta ctc gat      816
Gln Arg Thr Pro Glu Val Ala Arg Ser Arg Ala Thr Pro Leu Leu Asp
        260                 265                 270 atg ata gac act gca tta ttg aca aat ggt aca aca gaa aac agg tat      864
Met Ile Asp Thr Ala Leu Leu Thr Asn Gly Thr Thr Glu Asn Arg Tyr
        275                 280                 285 ggc ata aaa tta ccc gta tct ctg ttg ttt att gct ggt cat gat acc      912
Gly Ile Lys Leu Pro Val Ser Leu Leu Phe Ile Ala Gly His Asp Thr
        290                 295                 300 aat ctt gca aat tta agc ggg gct tta gat ctt aac tgg tcg cta ccc      960
Asn Leu Ala Asn Leu Ser Gly Ala Leu Asp Leu Asn Trp Ser Leu Pro
305                 310                 315                 320 ggt caa ccc gat aat acc cct cct ggt ggg gag ctt gta ttc gaa aag     1008
Gly Gln Pro Asp Asn Thr Pro Pro Gly Gly Glu Leu Val Phe Glu Lys
                325                 330                 335 tgg aaa aga acc agt gat aat acg gat tgg gtt cag gtt tca ttt gtt     1056
Trp Lys Arg Thr Ser Asp Asn Thr Asp Trp Val Gln Val Ser Phe Val
            340                 345                 350 tat cag acg ctg aga gat atg agg gat ata caa ccg ttg tcg tta gaa     1104
Tyr Gln Thr Leu Arg Asp Met Arg Asp Ile Gln Pro Leu Ser Leu Glu
        355                 360                 365 aaa cct gct ggc aaa gtt gat tta aaa tta att gca tgt gaa gag aaa     1152
Lys Pro Ala Gly Lys Val Asp Leu Lys Leu Ile Ala Cys Glu Glu Lys
370                 375                 380 aat agt cag gga atg tgt tcg tta aaa agt ttt tcc agg ctc att aag     1200
Asn Ser Gln Gly Met Cys Ser Leu Lys Ser Phe Ser Arg Leu Ile Lys
385                 390                 395                 400 gaa att cgc gtg cca gag tgt gca gtt acg gaa                         1233
Glu Ile Arg Val Pro Glu Cys Ala Val Thr Glu
                405                 410

<210> SEQ ID NO 2
<211> LENGTH: 411
<212> TYPE: PRT
<213> ORGANISM: Citrobacter braakii

<400> SEQUENCE: 2

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asn Val
            20                  25                  30

Thr Pro Asp Gln Trp Pro Gln Trp Asp Val Pro Leu Gly Trp Leu Thr
        35                  40                  45

Pro Arg Gly Gly Glu Leu Val Ser Glu Leu Gly Gln Tyr Gln Arg Leu
    50                  55                  60

Trp Phe Thr Ser Lys Gly Leu Leu Asn Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Ala Phe Leu Ala Gly Leu Ala Pro Lys Cys Gln Ile Gln Val
            100                 105                 110

His Tyr Gln Lys Asp Glu Glu Lys Asn Asp Pro Leu Phe Asn Pro Val
        115                 120                 125

Lys Met Gly Lys Cys Ser Phe Asn Thr Leu Gln Val Lys Asn Ala Ile
    130                 135                 140

Leu Glu Arg Ala Gly Gly Asn Ile Glu Leu Tyr Thr Gln Arg Tyr Gln
145                 150                 155                 160
```

-continued

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
            180                 185                 190

Leu Pro Ser Glu Leu Lys Val Thr Pro Asp Asn Val Ser Leu Pro Gly
        195                 200                 205

Ala Trp Ser Leu Ser Thr Leu Thr Glu Ile Phe Leu Leu Gln Glu
210                 215                 220

Ala Gln Gly Met Pro Gln Val Ala Trp Gly Arg Ile Thr Gly Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
            260                 265                 270

Met Ile Asp Thr Ala Leu Leu Thr Asn Gly Thr Thr Glu Asn Arg Tyr
        275                 280                 285

Gly Ile Lys Leu Pro Val Ser Leu Leu Phe Ile Ala Gly His Asp Thr
    290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Pro Gly Gly Glu Leu Val Phe Glu Lys
                325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
        355                 360                 365

Lys Pro Ala Gly Lys Val Asp Leu Lys Leu Ile Ala Cys Glu Glu Lys
    370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 3
<211> LENGTH: 411
<212> TYPE: PRT
<213> ORGANISM: Citrobacter braakii
<220> FEATURE:
<221> NAME/KEY: mat_peptide
<222> LOCATION: (1)..(411)

<400> SEQUENCE: 3

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asp Val
                20                  25                  30

Thr Pro Asp Gln Trp Pro Gln Trp Asp Val Pro Leu Gly Trp Leu Thr
            35                  40                  45

Pro Arg Gly Gly Glu Leu Val Ser Glu Leu Gly Gln Tyr Gln Arg Leu
        50                  55                  60

Trp Phe Thr Ser Lys Gly Leu Leu Asn Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Ala Phe Leu Ala Gly Leu Ala Pro Lys Cys Gln Ile Gln Val
            100                 105                 110

His Tyr Gln Lys Asp Glu Glu Lys Asn Asp Pro Leu Phe Asn Pro Val
            115                 120                 125

Lys Met Gly Lys Cys Ser Phe Asn Thr Leu Lys Val Lys Asn Ala Ile
130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
            165                 170                 175

Thr Cys Lys Thr Thr Glu Lys Ser Thr Lys Cys Thr Leu Pro Glu Ala
            180                 185                 190

Leu Pro Ser Glu Phe Lys Val Thr Pro Asp Asn Val Ser Leu Pro Gly
            195                 200                 205

Ala Trp Ser Leu Ser Ser Thr Leu Thr Glu Ile Phe Leu Leu Gln Glu
210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
            245                 250                 255

Gln Arg Thr Pro Glu Val Ala Arg Ser Arg Ala Thr Pro Leu Leu Asp
            260                 265                 270

Met Ile Asp Thr Ala Leu Leu Thr Asn Gly Thr Thr Glu Asn Arg Tyr
            275                 280                 285

Gly Ile Lys Leu Pro Val Ser Leu Leu Phe Ile Ala Gly His Asp Thr
290                 295                 300

Asn Leu Ala Asn Leu Ser Gly Ala Leu Asp Leu Lys Trp Ser Leu Pro
305                 310                 315                 320

Gly Gln Pro Asp Asn Thr Pro Pro Gly Gly Glu Leu Val Phe Glu Lys
            325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
            355                 360                 365

Lys Pro Ala Gly Lys Val Asp Leu Lys Leu Ile Ala Cys Glu Glu Lys
370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
            405                 410

<210> SEQ ID NO 4
<211> LENGTH: 411
<212> TYPE: PRT
<213> ORGANISM: Citronbacter freundii
<220> FEATURE:
<221> NAME/KEY: mat_peptide
<222> LOCATION: (1)..(411)

<400> SEQUENCE: 4

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asp Val
            20                  25                  30

Thr Pro Asp Gln Trp Pro Gln Trp Asp Val Pro Leu Gly Trp Leu Thr
            35                  40                  45

Pro Arg Gly Gly Glu Leu Val Ser Glu Leu Gly Gln Tyr Gln Arg Leu

```
                      50                  55                  60

Trp Phe Thr Ser Lys Gly Leu Leu Asn Asn Gln Thr Cys Pro Ser Pro
 65                  70                  75                  80

Gly Gln Val Ala Val Ile Ala Asp Thr Asp Gln Arg Thr Arg Lys Thr
                 85                  90                  95

Gly Glu Ala Phe Leu Ala Gly Leu Ala Pro Lys Cys Gln Ile Gln Val
            100                 105                 110

His Tyr Gln Lys Asp Glu Glu Lys Thr Asp Pro Leu Phe Asn Pro Val
        115                 120                 125

Lys Met Gly Thr Cys Ser Phe Asn Thr Leu Lys Val Lys Asn Ala Ile
    130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
            180                 185                 190

Leu Pro Ser Glu Leu Lys Val Thr Pro Asp Asn Val Ser Leu Pro Gly
        195                 200                 205

Ala Trp Ser Leu Ser Ser Thr Leu Thr Glu Ile Phe Leu Leu Gln Glu
    210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
            260                 265                 270

Met Ile Asp Thr Ala Leu Leu Thr Asn Gly Thr Thr Glu Asn Arg Tyr
        275                 280                 285

Gly Ile Lys Leu Pro Val Ser Leu Leu Phe Ile Ala Gly His Asp Thr
    290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Pro Gly Gly Glu Leu Val Phe Glu Lys
                325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
        355                 360                 365

Lys Pro Ala Gly Lys Val Asp Leu Lys Leu Ile Ala Cys Glu Glu Lys
    370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 5
<211> LENGTH: 1236
<212> TYPE: DNA
<213> ORGANISM: Artificial
<220> FEATURE:
<223> OTHER INFORMATION: Synthetic construct
<220> FEATURE:
<221> NAME/KEY: CDS
<222> LOCATION: (1)..(1233)
<220> FEATURE:
```

<221> NAME/KEY: mat_peptide
<222> LOCATION: (1)..(1233)
<220> FEATURE:
<221> NAME/KEY: misc_feature
<222> LOCATION: (18)..(18)
<223> OTHER INFORMATION: Xaa at position 18 is Gly
<220> FEATURE:
<221> NAME/KEY: misc_feature
<222> LOCATION: (323)..(323)
<223> OTHER INFORMATION: Xaa at position 323 is Pro

<400> SEQUENCE: 5

| gaa | gag | cag | aat | ggt | atg | aaa | ctt | gag | cgg | gtt | gtg | ata | gtg | agt | cgt | 48 |
|---|---|---|---|---|---|---|---|---|---|---|---|---|---|---|---|---|
| Glu | Glu | Gln | Asn | Gly | Met | Lys | Leu | Glu | Arg | Val | Val | Ile | Val | Ser | Arg | |
| 1 | | | | 5 | | | | | 10 | | | | | 15 | | |

| cat | ggr | gta | aga | gca | cct | acg | aag | ttc | act | cca | ata | atg | aaa | aat | gtc | 96 |
|---|---|---|---|---|---|---|---|---|---|---|---|---|---|---|---|---|
| His | Xaa | Val | Arg | Ala | Pro | Thr | Lys | Phe | Thr | Pro | Ile | Met | Lys | Asn | Val | |
| | | 20 | | | | | 25 | | | | | 30 | | | | |

| aca | ccc | gat | caa | tgg | cca | caa | tgg | gat | gtg | ccg | tta | gga | tgg | cta | acg | 144 |
|---|---|---|---|---|---|---|---|---|---|---|---|---|---|---|---|---|
| Thr | Pro | Asp | Gln | Trp | Pro | Gln | Trp | Asp | Val | Pro | Leu | Gly | Trp | Leu | Thr | |
| | | | 35 | | | | | 40 | | | | | 45 | | | |

| cct | cgt | ggg | gga | gaa | ctt | gtt | tct | gaa | tta | ggt | cag | tat | caa | cgt | tta | 192 |
|---|---|---|---|---|---|---|---|---|---|---|---|---|---|---|---|---|
| Pro | Arg | Gly | Gly | Glu | Leu | Val | Ser | Glu | Leu | Gly | Gln | Tyr | Gln | Arg | Leu | |
| 50 | | | | | 55 | | | | | 60 | | | | | | |

| tgg | ttc | acg | agc | aaa | ggt | ctg | ttg | aat | aat | caa | acg | tgc | cca | tct | cca | 240 |
|---|---|---|---|---|---|---|---|---|---|---|---|---|---|---|---|---|
| Trp | Phe | Thr | Ser | Lys | Gly | Leu | Leu | Asn | Asn | Gln | Thr | Cys | Pro | Ser | Pro | |
| 65 | | | | | 70 | | | | | 75 | | | | | 80 | |

| ggg | cag | gtt | gct | gtt | att | gca | gac | acg | gat | caa | cgc | acc | cgt | aaa | acg | 288 |
|---|---|---|---|---|---|---|---|---|---|---|---|---|---|---|---|---|
| Gly | Gln | Val | Ala | Val | Ile | Ala | Asp | Thr | Asp | Gln | Arg | Thr | Arg | Lys | Thr | |
| | | | | 85 | | | | | 90 | | | | | 95 | | |

| ggt | gag | gcg | ttt | ctg | gct | ggg | tta | gca | cca | aaa | tgt | caa | att | caa | gtg | 336 |
|---|---|---|---|---|---|---|---|---|---|---|---|---|---|---|---|---|
| Gly | Glu | Ala | Phe | Leu | Ala | Gly | Leu | Ala | Pro | Lys | Cys | Gln | Ile | Gln | Val | |
| | | | | 100 | | | | | 105 | | | | | 110 | | |

| cat | tat | cag | aag | gat | gaa | gaa | aaa | aat | gat | cct | ctt | ttt | aat | ccg | gta | 384 |
|---|---|---|---|---|---|---|---|---|---|---|---|---|---|---|---|---|
| His | Tyr | Gln | Lys | Asp | Glu | Glu | Lys | Asn | Asp | Pro | Leu | Phe | Asn | Pro | Val | |
| | | | 115 | | | | | 120 | | | | | 125 | | | |

| aaa | atg | ggg | aaa | tgt | tcg | ttt | aac | aca | ttg | cag | gtt | aaa | aac | gct | att | 432 |
|---|---|---|---|---|---|---|---|---|---|---|---|---|---|---|---|---|
| Lys | Met | Gly | Lys | Cys | Ser | Phe | Asn | Thr | Leu | Gln | Val | Lys | Asn | Ala | Ile | |
| | 130 | | | | | 135 | | | | | 140 | | | | | |

| ctg | gaa | cgg | gcc | gga | gga | aat | att | gaa | ctg | tat | acc | caa | cgc | tat | caa | 480 |
|---|---|---|---|---|---|---|---|---|---|---|---|---|---|---|---|---|
| Leu | Glu | Arg | Ala | Gly | Gly | Asn | Ile | Glu | Leu | Tyr | Thr | Gln | Arg | Tyr | Gln | |
| 145 | | | | | 150 | | | | | 155 | | | | | 160 | |

| tct | tca | ttt | cgg | acc | ctg | gaa | aat | gtt | tta | aat | ttc | tca | caa | tcg | gag | 528 |
|---|---|---|---|---|---|---|---|---|---|---|---|---|---|---|---|---|
| Ser | Ser | Phe | Arg | Thr | Leu | Glu | Asn | Val | Leu | Asn | Phe | Ser | Gln | Ser | Glu | |
| | | | | 165 | | | | | 170 | | | | | 175 | | |

| aca | tgt | aag | act | aca | gaa | aag | tct | acg | aaa | tgc | aca | tta | cca | gag | gct | 576 |
|---|---|---|---|---|---|---|---|---|---|---|---|---|---|---|---|---|
| Thr | Cys | Lys | Thr | Thr | Glu | Lys | Ser | Thr | Lys | Cys | Thr | Leu | Pro | Glu | Ala | |
| | | | 180 | | | | | 185 | | | | | 190 | | | |

| tta | ccg | tct | gaa | ctt | aag | gta | act | cct | gac | aat | gta | tca | tta | cct | ggt | 624 |
|---|---|---|---|---|---|---|---|---|---|---|---|---|---|---|---|---|
| Leu | Pro | Ser | Glu | Leu | Lys | Val | Thr | Pro | Asp | Asn | Val | Ser | Leu | Pro | Gly | |
| | | 195 | | | | | 200 | | | | | 205 | | | | |

| gcc | tgg | agt | ctt | tct | tcc | acg | ctg | act | gag | ata | ttt | ctg | ttg | caa | gag | 672 |
|---|---|---|---|---|---|---|---|---|---|---|---|---|---|---|---|---|
| Ala | Trp | Ser | Leu | Ser | Ser | Thr | Leu | Thr | Glu | Ile | Phe | Leu | Leu | Gln | Glu | |
| | 210 | | | | | 215 | | | | | 220 | | | | | |

| gcc | cag | gga | atg | cca | cag | gta | gcc | tgg | ggg | cgt | att | acg | gga | gaa | aaa | 720 |
|---|---|---|---|---|---|---|---|---|---|---|---|---|---|---|---|---|
| Ala | Gln | Gly | Met | Pro | Gln | Val | Ala | Trp | Gly | Arg | Ile | Thr | Gly | Glu | Lys | |
| 225 | | | | | 230 | | | | | 235 | | | | | 240 | |

| gaa | tgg | aga | gat | ttg | tta | agt | ctg | cat | aac | gct | cag | ttt | gat | ctt | ttg | 768 |
|---|---|---|---|---|---|---|---|---|---|---|---|---|---|---|---|---|
| Glu | Trp | Arg | Asp | Leu | Leu | Ser | Leu | His | Asn | Ala | Gln | Phe | Asp | Leu | Leu | |
| | | | | 245 | | | | | 250 | | | | | 255 | | |

| caa | aga | act | cca | gaa | gtt | gcc | cgt | agt | agg | gcc | aca | cca | tta | ctc | gat | 816 |
|---|---|---|---|---|---|---|---|---|---|---|---|---|---|---|---|---|
| Gln | Arg | Thr | Pro | Glu | Val | Ala | Arg | Ser | Arg | Ala | Thr | Pro | Leu | Leu | Asp | |

```
atg ata gac act gca tta ttg aca aat ggt aca aca gaa aac agg tat    864
Met Ile Asp Thr Ala Leu Leu Thr Asn Gly Thr Thr Glu Asn Arg Tyr
        275                 280                 285 ggc ata aaa tta ccc gta tct ctg ttg ttt att gct ggt cat gat acc    912
Gly Ile Lys Leu Pro Val Ser Leu Leu Phe Ile Ala Gly His Asp Thr
290                 295                 300 aat ctt gca aat tta agc ggg gct tta gat ctt aac tgg tcg cta ccc    960
Asn Leu Ala Asn Leu Ser Gly Ala Leu Asp Leu Asn Trp Ser Leu Pro
305                 310                 315                 320 ggt caa ccs gat aay acc ccg ccg ggc gac aag ctt gta ttc gaa aag    1008
Gly Gln Xaa Asp Asn Thr Pro Pro Gly Asp Lys Leu Val Phe Glu Lys
                325                 330                 335 tgg aaa aga acc agt gat aat acg gat tgg gtt cag gtt tca ttt gtt    1056
Trp Lys Arg Thr Ser Asp Asn Thr Asp Trp Val Gln Val Ser Phe Val
            340                 345                 350 tat cag acg ctg aga gat atg agg gat ata caa ccg ttg tcg tta gaa    1104
Tyr Gln Thr Leu Arg Asp Met Arg Asp Ile Gln Pro Leu Ser Leu Glu
        355                 360                 365 aaa cct gct ggc aaa gtt gat tta aaa tta att gca tgt gaa gag aaa    1152
Lys Pro Ala Gly Lys Val Asp Leu Lys Leu Ile Ala Cys Glu Glu Lys
370                 375                 380 aat agt cag gga atg tgt tcg tta aaa agt ttt tcc agg ctc att aag    1200
Asn Ser Gln Gly Met Cys Ser Leu Lys Ser Phe Ser Arg Leu Ile Lys
385                 390                 395                 400 gaa att cgc gtg cca gag tgt gca gtt acg gaa taa                    1236
Glu Ile Arg Val Pro Glu Cys Ala Val Thr Glu
                405                 410

<210> SEQ ID NO 6
<211> LENGTH: 411
<212> TYPE: PRT
<213> ORGANISM: Artificial
<220> FEATURE:
<221> NAME/KEY: misc_feature
<222> LOCATION: (18)..(18)
<223> OTHER INFORMATION: The 'Xaa' at location 18 stands for Gly.
<220> FEATURE:
<221> NAME/KEY: misc_feature
<222> LOCATION: (323)..(323)
<223> OTHER INFORMATION: The 'Xaa' at location 323 stands for Pro.
<220> FEATURE:
<223> OTHER INFORMATION: Synthetic Construct

<400> SEQUENCE: 6

Glu Glu Gln Asn Gly Met Lys Leu Glu Arg Val Val Ile Val Ser Arg
1               5                   10                  15

His Xaa Val Arg Ala Pro Thr Lys Phe Thr Pro Ile Met Lys Asn Val
            20                  25                  30

Thr Pro Asp Gln Trp Pro Gln Trp Asp Val Pro Leu Gly Trp Leu Thr
        35                  40                  45

Pro Arg Gly Gly Glu Leu Val Ser Glu Leu Gly Gln Tyr Gln Arg Leu
    50                  55                  60

Trp Phe Thr Ser Lys Gly Leu Leu Asn Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Ala Phe Leu Ala Gly Leu Ala Pro Lys Cys Gln Ile Gln Val
            100                 105                 110

His Tyr Gln Lys Asp Glu Glu Lys Asn Asp Pro Leu Phe Asn Pro Val
        115                 120                 125
```

Lys Met Gly Lys Cys Ser Phe Asn Thr Leu Gln Val Lys Asn Ala Ile
            130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
            180                 185                 190

Leu Pro Ser Glu Leu Lys Val Thr Pro Asp Asn Val Ser Leu Pro Gly
        195                 200                 205

Ala Trp Ser Leu Ser Ser Thr Leu Thr Glu Ile Phe Leu Leu Gln Glu
210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
            260                 265                 270

Met Ile Asp Thr Ala Leu Leu Thr Asn Gly Thr Thr Glu Asn Arg Tyr
        275                 280                 285

Gly Ile Lys Leu Pro Val Ser Leu Leu Phe Ile Ala Gly His Asp Thr
290                 295                 300

Asn Leu Ala Asn Leu Ser Gly Ala Leu Asp Leu Asn Trp Ser Leu Pro
305                 310                 315                 320

Gly Gln Xaa Asp Asn Thr Pro Pro Gly Asp Lys Leu Val Phe Glu Lys
                325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
        355                 360                 365

Lys Pro Ala Gly Lys Val Asp Leu Lys Leu Ile Ala Cys Glu Glu Lys
370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
                405                 410

<210> SEQ ID NO 7
<211> LENGTH: 66
<212> TYPE: DNA
<213> ORGANISM: Citrobacter braakii
<220> FEATURE:
<221> NAME/KEY: sig_peptide
<222> LOCATION: (1)..(66)
<220> FEATURE:
<221> NAME/KEY: CDS
<222> LOCATION: (1)..(66)

<400> SEQUENCE: 7 atg agt aca ttc atc att cgt tta tta ttt ttt tct ctc tta tgc ggt     48
Met Ser Thr Phe Ile Ile Arg Leu Leu Phe Phe Ser Leu Leu Cys Gly
1               5                   10                  15 tct ttc tca ata cat gct                                             66
Ser Phe Ser Ile His Ala
            20

<210> SEQ ID NO 8

```
<211> LENGTH: 22
<212> TYPE: PRT
<213> ORGANISM: Citrobacter braakii

<400> SEQUENCE: 8

Met Ser Thr Phe Ile Ile Arg Leu Leu Phe Ser Leu Leu Cys Gly
1               5                   10                  15

Ser Phe Ser Ile His Ala
            20

<210> SEQ ID NO 9
<211> LENGTH: 433
<212> TYPE: PRT
<213> ORGANISM: Citrobacter freundii
<220> FEATURE:
<221> NAME/KEY: mat_peptide
<222> LOCATION: (1)..(433)

<400> SEQUENCE: 9

Met Ser Thr Phe Ile Ile Arg Leu Leu Phe Ser Leu Leu Cys Gly
1               5                   10                  15

Ser Phe Ser Ile His Ala Glu Glu Pro Asn Gly Met Lys Leu Glu Arg
            20                  25                  30

Val Val Ile Val Ser Arg His Gly Val Arg Ala Pro Thr Lys Phe Thr
        35                  40                  45

Pro Ile Met Lys Asp Val Thr Pro Asp Gln Trp Pro Gln Trp Asp Val
50                  55                  60

Pro Leu Gly Trp Leu Thr Pro Arg Gly Gly Glu Leu Val Ser Glu Leu
65                  70                  75                  80

Gly Gln Tyr Gln Arg Leu Trp Phe Thr Ser Lys Gly Leu Leu Asn Asn
                85                  90                  95

Gln Thr Cys Pro Ser Pro Gly Gln Val Ala Val Ile Ala Asp Thr Asp
            100                 105                 110

Gln Arg Thr Arg Lys Thr Gly Glu Ala Phe Leu Ala Gly Leu Ala Pro
        115                 120                 125

Lys Cys Gln Ile Gln Val His Tyr Gln Lys Asp Glu Glu Lys Thr Asp
130                 135                 140

Pro Leu Phe Asn Pro Val Lys Met Gly Thr Cys Ser Phe Asn Thr Leu
145                 150                 155                 160

Lys Val Lys Asn Ala Ile Leu Glu Arg Ala Gly Gly Asn Ile Glu Leu
                165                 170                 175

Tyr Thr Gln Arg Tyr Gln Ser Ser Phe Arg Thr Leu Glu Asn Val Leu
            180                 185                 190

Asn Phe Ser Gln Ser Glu Thr Cys Lys Thr Thr Glu Lys Ser Thr Lys
        195                 200                 205

Cys Thr Leu Pro Glu Ala Leu Pro Ser Glu Leu Lys Val Thr Pro Asp
    210                 215                 220

Asn Val Ser Leu Pro Gly Ala Trp Ser Leu Ser Ser Thr Leu Thr Glu
225                 230                 235                 240

Ile Phe Leu Leu Gln Glu Ala Gln Gly Met Pro Gln Val Ala Trp Gly
                245                 250                 255

Arg Ile Thr Gly Glu Lys Glu Trp Arg Asp Leu Leu Ser Leu His Asn
            260                 265                 270

Ala Gln Phe Asp Leu Leu Gln Arg Thr Pro Glu Val Ala Arg Ser Arg
        275                 280                 285

Ala Thr Pro Leu Leu Asp Met Ile Asp Thr Ala Leu Leu Thr Asn Gly
    290                 295                 300
```

-continued

```
Thr Thr Glu Asn Arg Tyr Gly Ile Lys Leu Pro Val Ser Leu Leu Phe
305                 310                315                 320

Ile Ala Gly His Asp Thr Asn Leu Ala Asn Leu Ser Gly Ala Leu Asp
            325                 330                 335

Leu Asn Trp Ser Leu Pro Gly Gln Pro Asp Asn Thr Pro Pro Gly Gly
            340                 345                 350

Glu Leu Val Phe Glu Lys Trp Lys Arg Thr Ser Asp Asn Thr Asp Trp
            355                 360                 365

Val Gln Val Ser Phe Val Tyr Gln Thr Leu Arg Asp Met Arg Asp Ile
        370                 375                 380

Gln Pro Leu Ser Leu Glu Lys Pro Ala Gly Lys Val Asp Leu Lys Leu
385                 390                 395                 400

Ile Ala Cys Glu Glu Lys Asn Ser Gln Gly Met Cys Ser Leu Lys Ser
                405                 410                 415

Phe Ser Arg Leu Ile Lys Glu Ile Arg Val Pro Glu Cys Ala Val Thr
            420                 425                 430

Glu
```